United States Patent
Mosnier et al.

(10) Patent No.: US 9,605,046 B2
(45) Date of Patent: Mar. 28, 2017

(54) PROTEASE ACTIVATED RECEPTOR-1 (PAR1) DERIVED CYTOPROTECTIVE POLYPEPTIDES AND RELATED METHODS

(71) Applicants: THE SCRIPPS RESEARCH INSTITUTE, La Jolla, CA (US); Laurent O. Mosnier, San Diego, CA (US); John H. Griffin, Del Mar, CA (US)

(72) Inventors: Laurent O. Mosnier, San Diego, CA (US); John H. Griffin, Del Mar, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/356,692

(22) PCT Filed: Nov. 7, 2012

(86) PCT No.: PCT/US2012/000546
§ 371 (c)(1),
(2) Date: May 7, 2014

(87) PCT Pub. No.: WO2013/070256
PCT Pub. Date: May 16, 2013

(65) Prior Publication Data
US 2015/0045283 A1    Feb. 12, 2015

Related U.S. Application Data

(60) Provisional application No. 61/628,834, filed on Nov. 7, 2011.

(51) Int. Cl.
| | |
|---|---|
| A61K 38/00 | (2006.01) |
| A61P 5/00 | (2006.01) |
| C07K 14/705 | (2006.01) |
| A61K 38/17 | (2006.01) |

(52) U.S. Cl.
CPC ......... *C07K 14/705* (2013.01); *A61K 38/177* (2013.01); *A61K 38/00* (2013.01)

(58) Field of Classification Search
CPC ..... A61K 38/00; A61K 38/177; C07K 14/705
See application file for complete search history.

(56) References Cited

U.S. PATENT DOCUMENTS 7,074,765 B2 * 7/2006 Schmaier ............. C07K 5/0817
514/13.7

FOREIGN PATENT DOCUMENTS

JP    2002-010784    *  1/2002    ........... C07K 14/705

OTHER PUBLICATIONS

Machine translation for JP2002-010784, Jan. 2002, 48 pages.*

* cited by examiner

*Primary Examiner* — Marcela M Cordero Garcia
(74) *Attorney, Agent, or Firm* — Hugh Wang; Thomas Fitting

(57) ABSTRACT

The present invention provides novel PAR 1 derived cytoprotective oligopeptides or polypeptides which typically contain at least the first 4 N-terminal residues that are substantially identical to the corresponding N-terminal residues of $Met^1$-$Arg^{46}$ deleted human PAR 1 sequence. These cytoprotective oligopeptides or polypeptides are capable of activating PAR 1 and promoting PAR 1 cytoprotective signaling activities. The invention also provides engineered cells or transgenic non-human animals which harbor in their genome an altered PAR 1 gene that is resistant to cleavage at $Arg^{41}$ and/or $Arg^{46}$ residues. Additionally provided in the invention are methods of screening candidate compounds to identity additional cytoprotective compounds or cytoprotective proteases. The invention further provides therapeutic use or methods of employing a PAR 1 derived cytoprotective oligopeptide or polypeptide to treat conditions associated with tissue injuries or undesired apoptosis.

16 Claims, 8 Drawing Sheets

ID NO:2.

PROTEASE ACTIVATED RECEPTOR-1 (PAR1) DERIVED CYTOPROTECTIVE POLYPEPTIDES AND RELATED METHODS

CROSS REFERENCE TO RELATED APPLICATIONS

This application is a national stage filing in accordance with 35 U.S.C. §371 of International Patent Application No. PCT/US2012/000546, filed Nov. 7, 2012, which claims benefit to U.S. Provisional Patent Application Ser. No. 61/628,834, filed Nov. 7, 2011, each of which is incorporated by reference in its entirety.

STATEMENT OF GOVERNMENT SUPPORT

This invention was made with government support under HL087618 and HL052246 awarded by the National Institutes of Health. The government has certain rights in the invention.

BACKGROUND OF THE INVENTION

The protease-activated receptor 1 (PAR1) is a thrombin receptor which belongs to the class of G protein-coupled receptors (GCPR). PAR1 is expressed in various tissues, e.g., endothelial cells, smooth muscles cells, fibroblasts, neurons and human platelets. It is involved in cellular responses associated with hemostasis, proliferation, and tissue injury. PAR1 is known to be activated by proteases, notably by thrombin, by cleavage at $Arg^{41}$ or by peptides that mimic the new N-terminus created when cleavage at $Arg^{41}$ occurs. Such peptides are often referred to as Thrombin Receptor Activating Peptides (TRAP). Thrombin cleavage of PAR1 or treatment of cells with TRAP are generally proinflammatory and can often be deleterious to cells or animals.

Plasma Protein C is a serine protease zymogen and is known for its mild deficiency linked to venous thrombosis risk and severe deficiency linked to neonatal purpura fulminans. Activated Protein C (APC) exerts both anticoagulant activity via proteolytic inactivation of factors Va and VIIIa and cellular cytoprotective actions via direct initiation of cell signaling. Based on studies of engineered APC mutants and the use of genetically modified mice, APC's cell signaling actions are thought to drive murine APC's mortality reduction in sepsis models, neuroprotective actions in brain injury models, and nephroprotective effects in kidney injury models. These actions in vivo are generally suggested to involve multiple receptors (PAR1, endothelial protein C receptor (EPCR), PAR3, and CD11b), while in vitro studies implicate these receptors and potentially also other receptors (apoER2, beta1 and beta3 integrins, S1P1, and the angiopoietin/Tie-2 axis) for APC's cellular effects. Crosstalk among these receptors may permit a timely integration of APC-induced signaling which ultimately determines APC's effects on a specific cell and organ.

Modulation of PAR1-mediated signaling activities could have various therapeutic applications. There is a need in the art for better means for such therapeutic applications. The present invention addresses this and other related needs.

SUMMARY OF THE INVENTION

In one aspect, the present invention provides isolated polypeptides (including short oligopeptides and longer polypeptides) derived from protease activated receptor-1 (PAR1). These PAR1-derived cytoprotective polypeptides typically have at least the first 4 N-terminal residues that are substantially identical to the corresponding N-terminal residues of $Met^1$-$Arg^{46}$ deleted human PAR1 sequence (SEQ ID NO:2), a variant sequence or an ortholog sequence. In some related embodiments, the invention provides isolated polynucleotides or nucleic acid molecules that encode the PAR1 derived polypeptides disclosed herein, as well as expression vectors harboring such polynucleotides.

The PAR1 derived cytoprotective polypeptides or oligopeptides typically comprise from about 4 amino acid residues to about 350 amino acid residues in length. In some embodiments, the polypeptides (comprise from about 8 amino acid residues to about 60 amino acid residues in length. In some embodiments, the polypeptides have at least the first 6 N-terminal residues that are substantially identical to the corresponding N-terminal residues of SEQ ID NO:2. In some other embodiments, the polypeptides have at least the first 8 N-terminal residues that are substantially identical to the corresponding N-terminal residues of SEQ ID NO:2. In still some other embodiments, the polypeptides have at least the first 20 N-terminal residues that are at least 90% identical to the corresponding N-terminal residues of SEQ ID NO:2.

Some preferred cytoprotective polypeptides of the invention have the first 20 N-terminal residues as shown in SEQ ID NO:4 (NPNDKYEPFWEDEEKNESGL). Some of these polypeptides consist essentially of an amino acid sequence shown in any one of SEQ ID NOs:3, 4, and 14-20. Some other embodiments of the invention are directed to variant polypeptides or peptidomimetics that are derived from the preferred cytoprotective polypeptides exemplified herein. In some these embodiments, the variant polypeptides contain one or more conservatively substituted residues in the N-terminus relative to SEQ ID NO:2.

In another aspect, the invention provides modified or mutant protease activated receptor-1 (PAR1) molecules or fragments thereof. Relative to an unmodified or wildtype PAR1 (e.g., SEQ ID NO:1), the modified or mutant PAR1 molecules or fragments thereof comprise a missense mutation at residue $Arg^{46}$. Some of the modified or mutant PAR1 polypeptide or fragment thereof comprises an $Arg^{46}Gln$ missense mutation. In some embodiments, the modified or mutant PAR1 polypeptide or fragment thereof can additionally contain a missense mutation at residue $Arg^{41}$. For example, they can additionally harbor an $Arg^{41}Gln$ substitution. In some related embodiments, isolated polynucleotides or nucleic acid molecules encoding such modified or mutant PAR1 polypeptides or fragments thereof are provided in the invention.

In another aspect, the invention provides engineered host cells or transgenic non-human animals. These engineered host cells or transgenic non-human animals contain in their genome an altered or mutant protease activated receptor-1 (PAR1) gene. The altered or mutant PAR1 gene encodes a PAR1 molecule that is resistant to protease cleavage at $Arg^{46}$.

In still another aspect, the invention provides methods for identifying agents with cytoprotective activities for endothelial cells or other cells. These methods typically entail (1) contacting a candidate agent with a cell expressing a mutant PAR1 or a PAR1 fragment that is resistant to thrombin cleavage; (2) detecting cleavage at $Arg^{46}$ in the mutant PAR1 or the PAR1 fragment or detecting a PAR1 mediated cytoprotective signaling activity. In some of the methods, the employed mutant PAR1 or PAR1 fragment contains a point mutation at $Arg^{41}$, e.g., an $Arg^{41}Gln$ substitution. In some methods, the employed cell expressing the mutant PAR1 or PAR1 fragment is an endothelial cell. In some embodiments, the candidate agent is contacted with the cell in vivo via administration to a transgenic non-human animal.

Some of the screening methods of the invention employ candidate agents that are peptides, peptidomimetics or analog compounds. For example, the candidate agents to be screened in the methods can be variants, analogs or peptidomimetics derived from the polypeptide shown in SEQ ID NO:4. In some other screening methods, the employed candidate agents are proteases or variants thereof. In some of the screening methods, cytoprotective activity of the candidate agents is examined by monitoring their effect on promoting activation of the PI3K-Akt survival pathway or inhibition of apoptosis.

In yet another aspect, the invention provides methods of promoting cytoprotective activity for endothelial cells. These methods involve contacting the cells with a PAR1-derived cytoprotective polypeptide which has at least the first 4 N-terminal residues that are substantially identical to the corresponding N-terminal residues of $Met^1$-$Arg^{46}$ deleted human PAR1 sequence (SEQ ID NO:2). Some of these methods employ a PAR1-derived cytoprotective polypeptide which has at least the first 6 N-terminal amino acid residues that are at least 90% identical to the corresponding N-terminal residues of SEQ ID NO:2. Some of the methods are directed to providing cytoprotective activity to endothelial cells in vivo (i.e., cells present in a subject). For example, a PAR1 derived cytoprotective polypeptide of the invention can be administered to a subject to reduce mortality from adult severe sepsis or pediatric meningococcemia; to promote wound healing in diabetic ulcer; to treat injuries from ischemic stroke, neurotrauma, or other acute or chronic neurodegenerative conditions; to treat injuries from cardiac ischemia/reperfusion, hepatic ischemia/reperfusion, renal ischemia/reperfusion; to treat inflammatory lung injury or gastrointestinal injury; to treat flap necrosis in reconstructive surgery; to prolong survival following Ebola infection; or to reduce injury caused by radiation.

A further understanding of the nature and advantages of the present invention may be realized by reference to the remaining portions of the specification and claims.

DETAILED DESCRIPTION OF THE INVENTION

1. Overview

Figure 1:
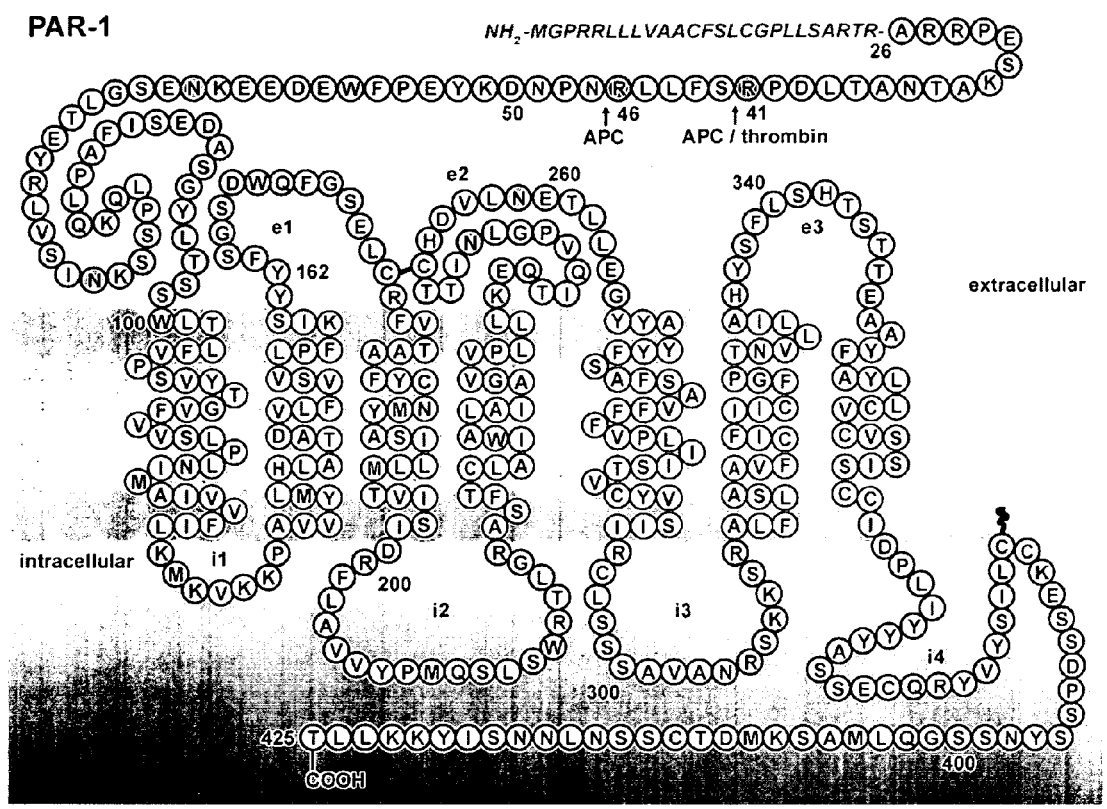
FIG. 1 is a schematic representation of the human PAR1 protein sequence (SEQ ID NO:1). As disclosed herein, the N-terminal domain is susceptible to proteolytic cleavage at $Arg^{41}$ or at $Arg^{46}$ after which the newly generated N-terminus which contains a free alpha-NH2 moiety at residues 42 or 47, respectively, that can act as a tethered-ligand which induces receptor activation resulting in the initiation and activation of intracellular G protein-coupled signaling pathways. In addition, the following sequence regions have been identified: three extracellular loops designated e1, e2 and e3, seven roughly parallel, transmembrane helices, and four intracellular domains designated i1, i2, i3 and i4 of which the latter is anchored into the inner membrane leaflet via a cysteine palmitoylation and which comprises the C-terminal end. Amino acid numbering starts with 1 at the methionine from the initiation codon. The mature PAR1 protein is likely to start at residue $Ala^{26}$.

The present invention is predicated in part on the discoveries by the present inventors that, in addition to the known cleavage site ($Arg^{41}$) in PAR1, Activated Protein C (APC) also cleaves PAR1 at a second cleavage site not previously known or envisioned in the art. Importantly, it was found that cleavage of PAR1 at the second site results in distinctly different consequences than caused by cleavage at the first site, and that this alternative cleavage distinguishes APC's from thrombin's effects. As detailed in the Examples below, the inventors first observed that APC cleaved a synthetic PAR1 N-terminal peptide (TR33-62; SEQ ID NO:13) at $Arg^{41}$, which is the same cleavage site by thrombin. It was then found that APC also cleaved the PAR1 TR33-62 peptide at an additional site distal from $Arg^{41}$. Proteolysis of the TR33-62 peptide with APC resulted in fragments corresponding to TR33-41 and TR42-62 similar to thrombin. But in contrast to thrombin, a third fragment was generated by APC and the TR42-62 fragment disappeared over time with the concomitant accumulation of a novel peptide. Incubation of thrombin-cleaved TR42-62 with APC resulted in proteolysis of TR42-62 and generation of the novel fragment of TR47-62, indicating the existence of a second APC cleavage site in PAR1 that was distinct and distal from $Arg^{41}$. Isolation of the novel proteolytic fragments and their MALDI-TOF analysis identified $Arg^{46}$ as the second APC cleavage site in the TR33-62 peptide or TR42-62 peptide.

Additionally, the inventors observed that, when cells containing wild-type EPCR were transfected with SEAP-PAR1 wild type and mutant constructs, both thrombin and APC cleaved wt-PAR1. As anticipated, efficient cleavage by thrombin was observed for R46Q-PAR1 but not R41Q-PAR1 or R41Q/R46Q-PAR1. In contrast, APC readily cleaved both R41Q-PAR1 and R46Q-PAR1 whereas cleavage of R41Q/R46Q-PAR1 by APC was negligible. APC mediated cleavage of R41Q-PAR1 and R46Q-PAR1 required the presence of functional EPCR and was not supported by the APC-binding-defective E86A-EPCR mutant. These results indicate that on cells $Arg^{46}$ in PAR1 can serve as a second cleavage site for APC. Since the new PAR1 N-terminus after proteolysis acts as a tethered ligand for receptor activation, cleavage at $Arg^{41}$ vs. $Arg^{46}$ could create structurally distinct agonists, which explains the divergent patterns for PAR1-mediated cytoprotective APC signaling vs. proinflammatory thrombin signaling.

The inventors further examined whether the APC-induced new PAR1 N-terminus starting at $Asn^{47}$ could promote signaling. It was found that a synthetic peptide with the PAR1 47-66 N-terminal sequence (SEQ ID NO:4) (termed "NPND", "TR47" or "TR47-66" peptide) increased Akt phosphorylation at $Ser^{473}$ in endothelial cells, whereas neither a control scrambled sequence (47-66)-peptide (SEQ ID NO:9) (termed "scrTR47" peptide) nor a TRAP peptide (SEQ ID NO:8) had a similar remarkable effect on Akt phosphorylation. Moreover, the NPND-peptide, but neither the scrambled sequence-related peptide nor a TRAP peptide, inhibited staurosporine-induced endothelial cell apoptosis. The inventors additionally demonstrated that TR47-66 induced vascular-endothelial protective effects in vitro and in vivo. These data suggest that the new N-terminus generated by APC's cleavage at $Arg^{46}$ in PAR1 generates a novel tethered ligand that can induce cytoprotective APC-like but not thrombin-like signaling characteristics.

In accordance with these discoveries, the present invention provides novel PAR1 derived cytoprotective peptides or polypeptides. These polypeptides are capable of activating cytoprotective signaling activities mediated by PAR1 as demonstrated by the TR47 peptide (SEQ ID NO:4) exemplified herein. The invention also provides engineered cells or transgenic non-human animals which harbor in their genome an altered PAR1 gene that is resistant to cleavage at one or both of the cleavage sites (i.e., Are and $Arg^{46}$ for human PAR1). Additionally provided in the invention are methods of screening candidate compounds to identity additional cytoprotective peptides or polypeptides, as well as screening methods for identifying proteases which are capable of activating the cytoprotective PAR1 signaling via cleaving PAR1 at the second cleavage site. The invention further provides therapeutic uses or methods of employing a PAR1 derived cytoprotective polypeptide to treat conditions associated with injuries or undesired apoptosis.

Unless otherwise stated, the present invention can be performed using standard procedures, as described, for example in Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954; Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2nd ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998). The following sections provide additional guidance for practicing the compositions and methods of the present invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: Oxford Dictionary of Biochemistry and Molecular Biology, Smith et al. (eds.), Oxford University Press (revised ed., 2000); Dictionary of Microbiology and Molecular Biology, Singleton et al. (Eds.), John Wiley & Sons (3PrdP ed., 2002); and A Dictionary of Biology (Oxford Paperback Reference), Martin and Hine (Eds.), Oxford University Press (4PthP ed., 2000). In addition, the following definitions are provided to assist the reader in the practice of the invention.

The singular terms "a," "an," and "the" include plural referents unless the context clearly indicates otherwise. Similarly, the word "or" is intended to include "and" unless the context clearly indicates otherwise.

As used herein, the term "amino acid" of a peptide refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The PAR1 derived protective polypeptides of the invention encompass derivative or analogs which have be modified with non-naturally coding amino acids.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, a "derivative" of a reference molecule (e.g., a cytoprotective polypeptide disclosed herein) is a molecule that is chemically modified relative to the reference molecule while substantially retaining the biological activity. The modification can be, e.g., oligomerization or polymerization, modifications of amino acid residues or peptide backbone, cross-linking, cyclization, conjugation, fusion to additional heterologous amino acid sequences, or other modifications that substantially alter the stability; solubility, or other properties of the peptide.

The term "engineered cell" or "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "fragment" refers to any peptide or polypeptide having an amino acid residue sequence shorter than that of a full-length polypeptide whose amino acid residue sequence is described herein. An isolated peptide of PAR1 is shortened or truncated compared to its parent full-length PAR1. Relative to a full length PAR1 sequence, the PAR1 derived cytoprotective polypeptides of the invention typically have N-terminus truncation at the conserved $Arg^{46}$-$Asn^{47}$ residues. These fragments can additionally contain C-terminus truncations (e.g., truncations of up to 50, 100, 200, 300 or more C-terminal residues) and/or also internal deletions.

The term "isolated" means the protein is removed from its natural surroundings. However, some of the components found with it may continue to be with an "isolated" protein. Thus, an "isolated polypeptide" is not as it appears in nature but may be substantially less than 100% pure protein.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Methods of alignment of sequences for comparison are well known in the art. Optimal alignment of sequences for comparison can be conducted, e.g., by the local homology algorithm of Smith and Waterman, Adv. Appl. Math. 2:482c, 1970; by the homology alignment algorithm of Needleman and Wunsch, J. Mol. Biol. 48:443, 1970; by the search for similarity method of Pearson and Lipman, Proc. Nat'l. Acad. Sci. USA 85:2444, 1988; by computerized implementations of these algorithms (GAP, BESTFIT, FASTA, and TFASTA in the Wisconsin Genetics Software Package, Genetics Computer Group, Madison, Wis.); or by manual alignment and visual inspection (see, e.g., Brent et al., *Current Protocols in Molecular Biology*, John Wiley & Sons, Inc. (ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

Unless otherwise specified, the terms "polypeptide" and "peptide" are used interchangeably herein (e.g., "PAR1 derived cytoprotective polypeptide" and "PAR1 derived cytoprotective peptide") to refer to a polymer of amino acid residues. They encompass both short oligopeptides (e.g., peptides with less than about 25 residues) and longer polypeptide molecules (e.g., polymers of more than about 25 or 30 amino acid residues). Typically, the PAR1 derived cytoprotective peptides (oligopeptides) or polypeptides of the invention can comprise from about 4 amino acid residues to about 350 or more amino acid residues in length. In some embodiments, the peptides or polypeptides comprise from about 8 amino acid residues to about 60 amino acid residues in length. The PAR1 derived cytoprotective peptides or polypeptides of the invention include naturally occurring amino acid polymers and non-naturally occurring amino acid polymer, as well as amino acid polymers in which one or more amino acid residue is an artificial chemical mimetic of a corresponding naturally occurring amino acid. Unless otherwise indicated, a particular polypeptide sequence also implicitly encompasses conservatively modified variants thereof.

As used herein, the term "peptide mimetic" or "peptidomimetic" refers to a derivative compound of a reference peptide (e.g., a cytoprotective polypeptide disclosed herein) that biologically mimics the peptide's functions. Typically, the peptidomimetic derivative of a PAR1 derived cytoprotective polypeptide of the invention has at least 50%, at least 75% or at least 90% of the cytoprotective activities (e.g., inhibition of endothelial cell apoptosis) of the reference polypeptide.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term "orthologs" or "homologs" refers to polypeptides that share substantial sequence identity and have the same or similar function from different species or organisms. For example, PAR1 from human, rabbit, rat, mouse and many other animal species are orthologs due to the similarities in their sequences and functions.

The phrase "signal transduction pathway" or "signaling activities" (e.g., the PAR1 mediated cytoprotective signaling) refers to at least one biochemical reaction, but more commonly a series of biochemical reactions, which result from interaction of a cell with a stimulatory compound or agent. Thus, the interaction of a stimulatory compound (e.g., PAR1 derived peptide shown in SEQ ID NO:4) with a cell generates a "signal" that is transmitted through the signal transduction pathway, ultimately resulting in a cellular response.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "transgene" means a nucleic acid sequence (e.g., one encoding a mutant PAR1 polypeptide of the invention) which has been introduced into a cell. A transgene could be partly or entirely heterologous, i.e., foreign, to the transgenic animal or cell into which it is introduced, or can be homologous to an endogenous gene of the transgenic animal or cell into which it is introduced. A transgene can also be present in a cell in the form of an episome. A transgene can include one or more transcriptional regulatory sequences and any other nucleic acid, such as 5' UTR sequences, 3' UTR sequences, or introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA.

As used herein, the term "treat" or treatment" refers to administration of compounds or agents to prevent or delay the onset of the symptoms, complications, or biochemical indicia of a disease or condition, alleviating the symptoms or arresting or inhibiting further development of the disease or condition, or disorder. Treatment may be prophylactic (to prevent or delay the onset of the condition, or to prevent the manifestation of clinical or subclinical symptoms thereof) or therapeutic suppression or alleviation of symptoms after the manifestation of the condition. For the therapeutic applications of the present invention, treatment is intended to reduce or alleviate at least one adverse effect or symptom in medical conditions that are associated with undesired cell death or tissue injuries. Examples of such conditions are described herein.

As used herein, the term "variant" refers to a molecule (e.g., a polypeptide or polynucleotide) that contains a sequence that is substantially identical to the sequence of a reference molecule. For example, the reference molecule can be an N terminally truncated PAR1 polypeptide (e.g., human PAR1 fragment starting at $Asn^{47}$ as shown in SEQ ID NO:2) or a polynucleotide encoding the polypeptide. The reference molecule can also be a PAR1 derived cytoprotective polypeptide disclosed herein or a polynucleotide encoding the cytoprotective polypeptide (e.g., TR47 as shown in SEQ ID NO:4). In some embodiments, the variant can share at least 50%, at least 70%, at least 80%, at least 90, at least 95% or more sequence identity with the reference molecule. In some other embodiments, the variant differs from the reference molecule by having one or more conservative amino acid substitutions. In some other embodiments, a variant of a reference molecule (e.g., a cytoprotective PAR1 polypeptide) has altered amino acid sequences (e.g., with one or more conservative amino acid substitutions) but substantially retains the biological activity of the reference molecule (e.g., activating PAR1 cytoprotective signaling). Conservative amino acid substitutions are well known to one skilled in the art.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

III. PAR-1 Derived Cytoprotective Polypeptides and Derivative Compounds

The invention provides cytoprotective polypeptides (including short peptides or oligopeptides) which are derived from PAR1. PAR1 sequences from human and many other non-human species have all been delineated in the art. For example, human PAR1 cDNA sequence, which has corresponding amino acid sequence shown in SEQ ID NO:1, was originally reported in Vu et al., Cell 64:1057-1068, 1991 with revisions noted in GenBank accession number NM_001992.3. The cytoprotective peptides or polypeptides of the invention are capable of activating PAR1-mediated cytoprotective signaling as disclosed herein. PAR-1 mediated cytoprotective signaling or signaling activity refers to any non-anticoagulant protective cellular activities mediated by the APC-PAR1 signaling pathway. These include activation of the PI3k-Akt survival pathway, inhibition of endothelial apoptosis (e.g., by blocking the pro-apoptotic activity of p53 or by other mechanisms), secretion of TNF-α by macrophages, reduction of cellular NFκB activation in endothelial cells, prevention of leukocyte adhesion to activated endothelial cells, induction of stabilization of endothelial cell barrier integrity via sphingosine-1 phosphate release or sphingosine-1 phosphate receptor 1 (S1P1) activation. As demonstrated in the Examples below, cytoprotective activities of the PAR1-derived polypeptides of the invention (e.g., SEQ ID NO:4) are evidenced by inhibition of apoptosis and promotion of cell survival.

Typically, the PAR1-derived cytoprotective polypeptides of the invention have at least the first 4 or 5 N-terminal residues that are substantially identical to the corresponding N-terminal residues of $Met^1$-$Arg^{46}$ deleted human PAR1 sequence (SEQ ID NO:2), variants (e.g., $Met^1$-$Arg^{46}$ deleted human PAR1 sequence with conservative substitutions) or orthologs (e.g., non-human PAR1 sequences with similar deletions). They can contain at least 4, 5, 6, 7, 8, 9, 10, 15, 20, 50, 100, 200, 300 or more amino acid residues in length. Some of the polypeptides comprise from about 4 amino acid residues to about 100 amino acid residues. Some of the polypeptides comprise from about 6 amino acid residues to about 50 amino acid residues. In some embodiments, the cytoprotective PAR1-derived polypeptide has at least the first 6 N-terminal residues that are substantially identical to the corresponding N-terminal residues of SEQ ID NO:2. In some other embodiments, the cytoprotective polypeptide has at least the first 7, 8, 9 or 10 N-terminal residues that are substantially identical to the corresponding N-terminal residues of SEQ ID NO:2. In still some other embodiments, the polypeptide has at least the first 10, 15, 20, 25, or more N-terminal residues that are substantially identical to the corresponding N-terminal residues of SEQ ID NO:2. In some preferred embodiments, the PAR1-derived cytoprotective peptides of the invention have at least the first 4, 5, 6, 7, 8, 9, 10, 15, 20 or more N-terminal residues that are 100% identical to the corresponding N-terminal residues of the truncated PAR1 sequence shown in SEQ ID NO:2. A few specific examples of the PAR 1-derived cytoprotective polypeptides of the invention are shown in SEQ ID NOs: 3 and 4, and also peptides NPNDKY (SEQ ID NO:14), NPNDKYEP (SEQ ID NO:15), NPNDKYEPFW (SEQ ID NO:16), NPNDKYEPFWED (SEQ ID NO:17), NPNDKYEPFWEDEE (SEQ ID NO:18), NPNDKYEPFWEDEEKN (SEQ ID NO:19), and NPNDKYEPFWEDEEKNES (SEQ ID NO:20).

As noted above, the PAR1-derived cytoprotective peptides or polypeptides also include peptides or polypeptides that are derived from variant sequences of the $Met^1$-$Arg^{46}$ deleted human PAR1 sequence or non-human PAR1 sequences. Thus, some of the cytoprotective polypeptides or the invention have at least the first 4 N-terminal residues which are substantially identical to the corresponding residues in the non-human PAR1 sequences which start at the conserved Asn residue. Based on alignment of human PAR1 extracellular fragment $Asn^{47}$-$Try^{100}$ (SEQ ID NO:3) with corresponding sequences from other species, the inventors observed that the sequence is extremely conserved in primates and has only moderate variation in different animals. Examples include PAR1 sequences from Rhesus monkey, white-tufted-ear marmoset, Northern white-cheeked gibbon, African savanna elephant, chimpanzee, dog, cattle, rat and mouse. In particular, it is known that $Arg^{46}$-$Asn^{47}$ residues of human PAR1 are conserved in various other non-human PAR1 orthologs. Alignment of various PAR1 ortholog sequences and the presence of the conserved Arg-Asn residues corresponding to $Arg^{46}$-$Asn^{47}$ of human PAR1 were also reported in the art, e.g., Soto et al., J. Biol. Chem. 285:18781-93, 2010. Thus, unless otherwise noted, the conserved residues bridging the second cleavage site in PAR1 as disclosed herein are referred to as $Arg^{46}$ and $Asn^{47}$ regardless of which species the PAR1 gene is from. It is understood that the precise positions of these two residues in a given PAR1 molecule is not necessarily at positions 46 and 47. Rather, the exact positions of these residues in a PAR1 polypeptide sequence can be easily determined by, e.g., sequence alignment. PAR1 sequences from the various non-human animals which contain this conserved cleavage site and a N-terminal sequence substantially identical to the human PAR1 sequence can all be readily employed in the practice of the present invention. Examples include, e.g., mouse PAR1 (Accession No. NM_010169.3), rat PAR1 (Acc. No. NM_012950.2) and dog PAR1 (Acc. No. XM_546059.2).

Cytoprotective compounds of the invention also encompass variants, analogs, peptidomimetics or other derivative compounds that can be generated from the PAR1 derived cytoprotective polypeptides exemplified herein (e.g., peptide TR47 as shown in SEQ ID NO:4). These derivative compounds can be subject to the screening methods described below to identify cytoprotective compounds with optimized activities. In some embodiments, the derivative compounds are modified versions of the exemplified peptides which are generated by conservative amino acid substitutions. For example, conservatively modified variants of polypeptide NPND KYEPFWEDEE KNESGL (SEQ ID NO:4) include polypeptides NPND RYEPFWEDEEKNESGL (SEQ ID NO:5), NPNDKYEPFWEEDEEKNESGL (SEQ ID NO:6) and NPND RYEPFWEDEDKNESGL (SEQ ID NO:7). In some other embodiments, the derivative compounds are variants produced by non-conservative substitutions to the extent that that they substantially retain the activities of those peptides. Modification to a cytoprotective PAR1 peptide of the invention can be performed with standard techniques routinely practiced in the art (e.g., U.S. Patent Applications 20080090760 and 20060286636).

In some embodiments, the analogs or derivative compounds of an exemplified PAR1-derived cytoprotective polypeptide of the invention (e.g., SEQ ID NO:4) can contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by polypeptide bonds. Similarly, they can also be cyclic polypeptides and other conformationally constrained structures. Methods for modifying a polypeptide to generate analogs and derivatives are well known in the art, e.g., Roberts and Vellaccio, *The Peptides: Analysis, Synthesis, Biology*, Eds. Gross and Meinhofer, Vol. 5, p. 341, Academic Press, Inc., New York, N.Y. (1983); and *Burger's Medicinal Chemistry and Drug Discovery*, Ed. Manfred E. Wolff, Ch. 15, pp. 619-620, John Wiley & Sons Inc., New York, N.Y. (1995).

Some other derivative compounds of the exemplified PAR1-derived cytoprotective polypeptides are peptidomimetics. Peptidomimetics based on a PAR1-derived cytoprotective polypeptide (e.g., SEQ ID NO:4) substantially retain the activities of the reference polypeptide. They include chemically modified polypeptides, polypeptide-like molecules containing non-naturally occurring amino acids, peptoids and the like, have a structure substantially the same as the reference polypeptides upon which the peptidomimetic is derived (see, for example, *Burger's Medicinal Chemistry and Drug Discovery,* 1995, supra). For example, the peptidomimetics can have one or more residues chemically derivatized by reaction of a functional side group. In addition to side group derivatizations, a chemical derivative can have one or more backbone modifications including alpha-amino substitutions such as N-methyl, N-ethyl, N-propyl and the like, and alpha-carbonyl substitutions such as thioester, thioamide, guanidino and the like. Typically, a peptidomimetic shows a considerable degree of structural identity when compared to the reference polypeptide and exhibits characteristics which are recognizable or known as being derived from related to the reference polypeptide. Peptidomimetics include, for example, organic structures which exhibit similar properties such as charge and charge spacing characteristics of the reference polypeptide. Peptidomimetics also can include constrained structures so as to maintain optimal spacing and charge interactions of the amino acid functional groups.

In some other embodiments, the PAR1-derived cytoprotective polypeptides described herein can be dimerized or multimerized by covalent attachment to at least one linker moiety. For example, the peptides or polypeptides can be conjugated with a $C_{1-12}$ linking moiety optionally terminated with one or two —NH—0 linkages and optionally substituted at one or more available carbon atoms with a lower alkyl substituent. The PAR1 derived peptides described herein can be joined by other chemical bond linkages, such as linkages by disulfide bonds or by chemical bridges. In some other embodiments, the cytoprotective peptides described herein can be linked physically in tandem to form a polymer of PAR1-derived peptides. The peptides making up such a polymer can be spaced apart from each other by a peptide linker. In some embodiments, molecular biology techniques well known in the art can be used to create a polymer of PAR1 peptides. In some embodiments, polyethylene glycol (PEG) may serve as a linker that dimerizes two peptide monomers. For example, a single PEG moiety containing two reactive functional groups may be simultaneously attached to the N-termini of both peptide chains of a peptide dimer. These peptides are referred to herein as "PEGylated peptides." In some embodiments, the peptide monomers of the invention may be oligomerized using the biotin/streptavidin system.

Methods for stabilizing peptides known in the art may be used with the methods and compositions described herein. For example, using D-amino acids, using reduced amide bonds for the peptide backbone, and using non-peptide bonds to link the side chains, including, but not limited to, pyrrolinone and sugar mimetics can each provide stabilization. The design and synthesis of sugar scaffold peptide mimetics are described in the art, e.g., Hirschmann et al., J. Med. Chem. 36, 2441-2448, 1996. Further, pyrrolinone-based peptide mimetics present the peptide pharmacophore on a stable background that has improved bioavailability characteristics (see, e.g., Smith et al., J. Am. Chem. Soc. 122, 11037-11038, 2000).

In some embodiment, derivative compounds of the exemplified cytoprotective PAR1 polypeptides include modifications within the sequence, such as, modification by terminal-$NH_2$ acylation, e.g., acetylation, or thioglycolic acid amidation, by terminal-carboxylamidation, e.g., with ammonia, methylamine, and the like terminal modifications. One can also modify the amino and/or carboxy termini of the polypeptides described herein. Terminal modifications are useful to reduce susceptibility by proteinase digestion, and therefore can serve to prolong half-life of the polypeptides in solution, particularly in biological fluids where proteases may be present. Amino terminus modifications include methylation (e.g., —$NHCH_3$ or —$N(CH_3)_2$), acetylation (e.g., with acetic acid or a halogenated derivative thereof such as α-chloroacetic acid, α-bromoacetic acid, or α-iodoacetic acid), adding a benzyloxycarbonyl (Cbz) group, or blocking the amino terminus with any blocking group containing a carboxylate functionality defined by RCOO— or sulfonyl functionality defined by R—$SO_2$—, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound. In some embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the peptides described herein, or incorporate a desamino or descarboxy residue at the termini of the peptide, so that there is no terminal amino or carboxyl group, to decrease susceptibility to proteases or to restrict the conformation of the peptide. Methods of circular peptide synthesis are known in the art, for example, in U.S. Patent Application No. 20090035814; and Muralidharan and Muir, Nat. Methods, 3:429-38, 2006. C-terminal functional groups of the peptides described herein include amide, amide lower alkyl, amide di(lower alkyl), lower alkoxy, hydroxy, and carboxy, and the lower ester derivatives thereof, and the pharmaceutically acceptable salts thereof.

The PAR1 derived cytoprotective polypeptide compounds described herein also serve as structural models for non-peptidic compounds with similar biological activity. There are a variety of techniques available for constructing compounds with the same or similar desired biological activity as the PAR1 peptides, but with more favorable activity than the PAR1 peptide with respect to solubility, stability, and susceptibility to hydrolysis and proteolysis. See, e.g., Morgan and Gainor, Ann. Rep. Med. Chem. 24:243-252, 1989. These techniques include, but are not limited to, replacing the peptide backbone with a backbone composed of phosphonates, amidates, carbamates, sulfonamides, secondary amines, and N-methylamino acids.

IV. Synthesis of PAR1 Derived Cytoprotective Polypeptides and Related Compounds

The PAR1 derived cytoprotective polypeptides described herein, including variants and derivatives thereof, can be chemically synthesized and purified by standard chemical or biochemical methods that are well known in the art. Some of the methods for generating analog or derivative compounds of the PAR1 derived cytoprotective polypeptides are described above. Other methods that may be employed for producing the cytoprotective polypeptides of the invention and their derivative compounds, e.g., solid phase peptide synthesis, are discussed below. For example, the peptides can be synthesized using t-Boc (tert-butyloxycarbonyl) or FMOC (9-flourenylmethloxycarbonyl) protection group described in the art. See, e.g., "Peptide synthesis and applications" in Methods in molecular biology Vol. 298, Ed. by John Howl; "Chemistry of Peptide Synthesis" by N. Leo Benoiton, 2005, CRC Press, (ISBN-13: 978-1574444544); and "Chemical Approaches to the Synthesis of Peptides and Proteins" by P. Lloyd-Williams, et. al., 1997, CRC-Press, (ISBN-13: 978-0849391422), Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954.

Solid phase peptide synthesis, developed by R. B. Merrifield, 1963, J. Am. Chem. Soc. 85 (14): 2149-2154, was a major breakthrough allowing for the chemical synthesis of peptides and small proteins. An insoluble polymer support (resin) is used to anchor the peptide chain as each additional alpha-amino acid is attached. This polymer support is constructed of 20-50 µm diameter particles which are chemically inert to the reagents and solvents used in solid phase peptide synthesis. These particles swell extensively in solvents, which makes the linker arms more accessible. Organic linkers attached to the polymer support activate the resin sites and strengthen the bond between the alpha-amino acid and the polymer support. Chloromethyl linkers, which were developed first, have been found to be unsatisfactory for longer peptides due to a decrease in step yields. The PAM (phenylacetamidomethyl) resin, because of the electron withdrawing power of the acid amide group on the phenylene ring, provides a much more stable bond than the classical resin. Another alternative resin for peptides under typical peptide synthesis conditions is the Wang resin. This resin is generally used with the FMOC labile protecting group.

A labile group protects the alpha-amino group of the amino acid. This group is easily removed after each coupling reaction so that the next alpha-amino protected amino acid may be added. Typical labile protecting groups include t-Boc (tert-butyloxycarbonyl) and FMOC. t-Boc is a very satisfactory labile group which is stable at room temperature and easily removed with dilute solutions of trifluoroacetic acid (TFA) and dichloromethane. FMOC is a base labile protecting group which is easily removed by concentrated solutions of amines (usually 20-55% piperidine in N-methylpyrrolidone). When using FMOC alpha-amino acids, an acid labile (or base stable) resin, such as an ether resin, is desired.

The stable blocking group protects the reactive functional group of an amino acid and prevents formation of complicated secondary chains. This blocking group must remain attached throughout the synthesis and may be removed after completion of synthesis. When choosing a stable blocking group, the labile protecting group and the cleavage procedure to be used should be considered. After generation of the resin bound synthetic peptide, the stable blocking groups are removed and the peptide is cleaved from the resin to produce a "free" peptide. In general, the stable blocking groups and organic linkers are labile to strong acids such as TFA. After the peptide is cleaved from the resin, the resin is washed away and the peptide is extracted with ether to remove unwanted materials such as the scavengers used in the cleavage reaction. The peptide is then frozen and lyophilized to produce the solid peptide. This is generally then characterized by HPLC and MALDI before being used. In addition, the peptide should be purified by HPLC to higher purity before use.

Commercial peptide synthesizing machines are available for solid phase peptide synthesis. For example, the Advanced Chemtech Model 396 Multiple Peptide Synthesizer and an Applied Biosystems Model 432A Peptide synthesizer are suitable. There are commercial companies that make custom synthetic peptides to order, e.g., Abbiotec, Abgent, AnaSpec Global Peptide Services, LLC., Invitrogen, and rPeptide, LLC.

The PAR1 derived cytoprotective polypeptides and derivatives thereof can also be synthesized and purified by molecular methods that are well known in the art. Recombinant polypeptides may be expressed in bacteria, mammal, insect, yeast, or plant cells. For example, conventional polymerase chain reaction (PCR) cloning techniques can be used to clone a polynucleotide encoding a PAR1 peptide or polypeptide, using the full length PAR1 cDNA sequence as the template for PCR Cloning. Alternatively, the sense and anti-sense strand of the coding nucleic acid can be made synthetically and then annealed together to form the double-stranded coding nucleic acid. Ideally, restriction enzyme digestion recognition sites should be designed at the ends of the sense and anti-sense strand to facilitate ligation into a cloning vector or other vectors. Alternatively, a 3'A-overhang can be include for the purpose of TA-cloning that is well known in the art. Such coding nucleic acids with 3'A-overhangs can be easily ligated into the Invitrogen topoisomerase-assisted TA vectors such as pCR®-TOPO, pCR®-Blunt II-TOPO, pENTR/D-TOPO®, and pENTR/SD/D-TOPO®. The coding nucleic acid can be cloned into a general purpose cloning vector such as pUC19, pBR322, pBluescript vectors (Stratagene Inc.) or pCR TOPO® from Invitrogen Inc. The resultant recombinant vector carrying the polynucleotide encoding a PAR1 peptide can then be used for further molecular biological manipulations such as site-directed mutagenesis for variant PAR1 peptide and/or to reduce the immunogenic properties of the peptide or improve protein expression in heterologous expression systems, or can be subcloned into protein expression vectors or viral vectors for the synthesis of fusion protein comprising PAR1 peptides and protein synthesis in a variety of protein expression systems using host cells selected from the group consisting of mammalian cell lines, insect cell lines, yeast, bacteria, and plant cells.

In some related embodiments, the invention provides isolated or substantially purified polynucleotides (DNA or RNA) which encode the PAR1-derived cytoprotective polypeptides described herein. Expression vectors and engineered host cells harboring the vectors for expressing polynucleotides encoding the polypeptides are also provided in the invention. The polynucleotide encoding a PAR1-derived cytoprotective polypeptide (e.g., peptide shown in SEQ ID NO:4) are operationally linked to a promoter in the expression vectors. The expression construct can further comprise a secretory sequence to assist purification of the peptide from the cell culture medium. The host cells to which the vectors are introduced can be any of a variety of expression host cells well known in the art, e.g., bacteria (e.g., E. coli), yeast cell, or mammalian cells.

Recombinant protein expression in different host cells can be constitutive or inducible with inducers such as copper sulfate, or sugars such as galactose, methanol, methylamine, thiamine, tetracycline, or IPTG. After the protein is expressed in the host cells, the host cells are lysed to liberate the expressed protein for purification. A preferred purification method is affinity chromatography such as ion-metal affinity chromatograph using nickel, cobalt, or zinc affinity resins for histidine-tagged PAR1 peptide. Methods of purifying histidine-tagged recombinant proteins are described by Clontech using their Talon® cobalt resin and by Novagen in their pET system manual, 10th edition. Another preferred purification strategy is by immuno-affinity chromatography, for example, anti-Myc antibody conjugated resin can be used to affinity purify Myc-tagged PAR1 peptide. Enzymatic digestion with serine proteases such as thrombin and enterokinase cleave and release the PAR1 peptide from the histidine or Myc tag, releasing the recombinant PAR1 peptide from the affinity resin while the histidine-tags and Myc-tags are left attached to the affinity resin.

Cell-free expression systems can also be used for producing cytoprotective PAR1 polypeptides of the invention. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix. An example of a cell-free translation system capable of producing proteins in high yield is described by Spirin et. al., Science 242:1162, 1988. The method uses a continuous flow design of the feeding buffer which contains amino acids, adenosine triphosphate (ATP), and guanosine triphosphate (GTP) throughout the reaction mixture and a continuous removal of the translated polypeptide product. The system uses *E. coli* lysate to provide the cell-free continuous feeding buffer. This continuous flow system is compatible with both prokaryotic and eukaryotic expression vectors. An example of large scale cell-free protein production is described in Chang et. al., Science 310:1950-3, 2005.

Other commercially available cell-free expression systems include the Expressway™ Cell-Free Expression Systems (Invitrogen) which utilize an *E. coli*-based in-vitro system for efficient, coupled transcription and translation reactions to produce up to milligram quantities of active recombinant protein in a tube reaction format; the Rapid Translation System (RTS) (Roche Applied Science) which also uses an *E. coli*-based in-vitro system; and the TNT Coupled Reticulocyte Lysate Systems (Promega) which uses a rabbit reticulocyte-based in-vitro system.

V. PAR1 with Altered Protease Cleavage Sites and Related Cells or Non-Human Animals The present invention provides modified or mutant protease activated receptor-1 (PAR1) molecules or fragments thereof which have altered protease cleavage sites. Relative to an unmodified or wildtype PAR1 (e.g., SEQ ID NO:1), the modified or mutant protease activated receptor-1 (PAR1) molecules or fragments thereof are resistant to protease (e.g., APC) cleavage at the first cleavage site (i.e., $Arg^{41}$), at the second cleavage site (i.e., $Arg^{46}$), or at both cleavage sites. As exemplified in the Examples below, these modified PAR1 molecules or fragments typically contain a missense substitution at one or both of the cleavage sites. For example, some of the modified or mutant PAR1 molecules or fragments thereof contain an $Arg^{46}Gln$ missense mutation. In some other embodiments, the modified or mutant PAR1 molecules or fragments thereof contain an $Arg^{41}Gln$ missense mutation. In still some other embodiments, the modified or mutant PAR1 molecules or fragments thereof contain both $Arg^{41}Gln$ and $Arg^{46}Gln$ substitutions. Other examples include Ala substitutions at positions 41 and/or 46. In related embodiments, isolated polynucleotides or nucleic acid molecules encoding such modified or mutant PAR1 polypeptides or fragments thereof (e.g., a modified PAR1 gene described below), as well as vectors harboring such polynucleotides are also provided in the invention. The modified PAR1 molecules or fragments of the invention with altered protease cleavage sites, the related polynucleotides and vectors can all be generated with routinely practiced techniques of biochemistry and molecular biology described herein or the specific procedures detailed in the Examples below.

The invention further provides engineered cells and transgenic non-human animals which contain a modified PAR1 gene in the genome. Typically, the PAR1 gene in the genome of the engineered cells or transgenic animals contains mutations that result in resistance to cleavage by proteases such as thrombin or APC. In some embodiments, the mutation renders the encoded PAR1 resistant to thrombin cleavage at the first cleavage site (i.e., cleavage at $Arg^{41}$) but not resistant to APC cleavage at the second cleavage site (i.e., $Arg^{46}$). For example, the altered PAR1 gene can harbor a missense mutation at the codon for $Arg^{41}$, e.g., $Arg^{41}Gln$ mutation. In some other embodiments, the modified PAR1 gene in the genome of the cells or animals is resistant to APC cleavage. For example, the PAR1 gene can have missense mutations at both $Arg^{41}$ and $Arg^{46}$. In still some other embodiments, the engineered cells or transgenic animals can harbor a modified PAR1 gene which encodes a PAR1 protein that is resistance to cleavage at $Arg^{46}$ but not at $Arg^{41}$.

The engineered cells harboring a mutant PAR1 gene described above can be generated from any cell suitable for expressing a PAR polypeptide. Preferably, the engineered cells are generated with a cell which naturally expresses PAR1 (e.g., an endothelial cell as exemplified in the Examples below). The transgenic non-human animals which harbor a mutant PAR1 gene described above can be generated from any animal suitable for transgene expression (e.g., mouse or rat). In some preferred embodiments, the transgenic non-human animals are transgenic mice. The engineered host cells and transgenic non-human animals which harbor a mutant PAR1 gene described above include cells or animals with mutations in the endogenous PAR1 gene, as well as cells or animals which contain an exogenous PAR1 mutant gene described herein (e.g., a mutant human PAR1 gene). Non-human animals that are either homozygous or heterozygous for the mutation in the PAR1 gene are included in the invention. Preferably, the animal is homozygous for the mutation.

The engineered host cells or non-human animals harboring a mutant PAR1 gene of the present invention can be generated using routinely practiced methods well known in the art or exemplified herein. Typically, they can be obtained by genetic manipulation. In some embodiments of the invention, non-human animals harboring a desired PAR1 mutant gene are created by genetic alteration of the wildtype PAR1 gene in a non-human animal, e.g., by targeted mutagenesis. Such gene targeting methods have been well described in the art for generating non-human animals that contain specific gene mutations, e.g., U.S. Pat. No. 6,284,944. Briefly, the first step in producing a gene-targeted non-human mammal is to prepare a DNA targeting vector. The targeting vector is designed to replace, via homologous recombination, part of the endogenous PAR1 gene sequence of a non-human mammal, so as to introduce the desired mutation (e.g., $Arg^{46}Gln$ substitution). The targeting vector is used to transfect non-human mammalian cell, e.g., a pluripotent, murine embryo-derived stem ("ES") cell. In the cell, homologous recombination (i.e., the gene-targeting event) takes place between the targeting vector and the target gene. The mutant cell is then used to produce intact non-human mammals (e.g., by aggregation of murine ES cells to mouse embryos) to generate germ-line chimeras. The germline chimeras are used to produce siblings heterozygous for the mutated targeted gene. Finally, interbreeding of heterozygous siblings yields non-human mammals (e.g., mice) homozygous for the mutated target gene.

Targeting vectors for the practice of this invention can be constructed using materials, information and processes known in the art. A general description of the targeting vector used in this invention follows. A targeting vector or replacement vector for use in this invention has two essential functions: (1) to integrate specifically (and stably) at the endogenous PAR1 target gene; and (2) to replace a portion of the endogenous PAR1 gene, thereby introducing the desired mutation around the Arg$^{46}$ and/or Arg$^{41}$ residues. Those two essential functions depend on two basic structural features of the targeting vector. The first basic structural feature of the targeting vector is a pair of regions, known as "arms of homology", which are homologous to selected regions of the endogenous PAR1 gene or regions flanking the PAR1 gene. This homology causes at least part of the targeting vector to integrate into the chromosome, replacing part or all of the PAR1 target gene, by homologous recombination. The second basic structural feature of the targeting vector consists of the actual base changes (mutations) to be introduced into the target gene. The mutation(s) to be introduced into the PAR1 target gene must be located within the "arms of homology."

Gene targeting, which affects the structure of a specific endogenous gene in a cell, is to be distinguished from other forms of stable transformation, wherein integration of exogenous DNA for expression in a transformed cell is not site-specific, and thus does not predictably affect the structure of any particular gene already in the transformed cell. Furthermore, with the type of targeting vector preferred in the practice of this invention, a reciprocal exchange of genomic DNA takes place (between the "arms of homology" and the target gene), and chromosomal insertion of the entire vector is advantageously avoided.

Various targeting vectors can be employed to practice the present invention. For a given vector, the length of the arms of homology that flank the replacement sequence can vary considerably without significant effect on the practice of the invention. The arms of homology must be of sufficient length four effective heteroduplex formation between one strand of the targeting vector and one strand of a transfected cell's chromosome, at the PAR1 target gene locus. The base pairs to be changed in the PAR1 target gene must lie within the sequence that constitutes the arms of homology. The arms of homology may lie within the PAR1 target gene, but it is not necessary that they do so and they may flank the PAR1 target gene.

Preferably, the targeting vector will comprise, between the arms of homology, a positive selection marker. The positive selection marker should be placed within an intron of the target gene, so that it will be spliced out of mRNA and avoid the expression of a target/marker fusion protein. More preferably the targeting vector will comprise two selection markers; a positive selection marker, located between the arms of homology, and a negative selection marker, located outside the arms of homology. The negative selection marker is a means of identifying and eliminating clones in which the targeting vector has been integrated into the genome by random insertion instead of by homologous recombination. Exemplary positive selection markers are neomycin phosphotransferase and hygromycin β phosphotransferase genes. Exemplary negative selection markers are Herpes simplex thymidine kinase and diphtheria toxin genes.

To eliminate potential interference on expression of the target protein, the positive selection marker can be flanked by short loxP recombination sites isolated from bacteriophage P1 DNA. Recombination between the two loxP sites at the targeted gene locus can be induced by introduction of cre recombinase to the cells. This results in the elimination of the positive selection marker, leaving only one of the two short loxP sites (see, e.g., U.S. Pat. No. 4,959,317). Excision of the positive selectable marker from the mutated PAR1 gene can thus be effected.

If base pair changes (mutations) are introduced into one of the arms of homology, it is possible for these changes to be incorporated into the cellular gene as a result of homologous recombination. Whether or not the mutations are incorporated into cellular DNA as a result of homologous recombination depends on where the crossover event takes place in the arm of homology bearing the changes. For example, the crossover in the arm occurs proximal to the mutations and so they are not incorporated into cellular DNA. In another scenario, the crossover takes place distal to the position of the mutations and they are incorporated into cellular DNA. Because the location of the crossover event is random, the frequency of homologous recombination events that include the mutations is increased if they are placed closer to the positive selection marker.

By the above method, the skilled artisan can achieve the incorporation of the selectable marker at a preselected location in the PAR1 target gene flanked by specific base pair changes. Presumably, the artisan would preferably choose to have the selectable marker incorporated within the intron of the target gene so as not to interfere with endogenous gene expression while the mutations would be included in adjacent coding sequence so as to make desired changes in the protein product of interest. See Askew et al., Mol. Cell. Biol. 13: 4115-4124, 1993; Fiering et al., Proc. Natl. Acad. Sci. USA 90: 8469-8473, 1993; Rubinstein et al., Nuc. Acid Res. 21: 2613-2617, 1993; Gu et al., Cell 73: 1155-1164, 1993; and Gu, et al., Science 265: 103-106, 1994).

In addition to non-human animals which have its endogenous PAR1 gene mutated in accordance with the present invention, transgenic animals harboring a heterologous PAR1 mutant gene are also included in the present invention. For example, a transgenic non-human animal of the present invention can be a mouse which contains a transgene which encodes a human PAR1 mutant gene. Typically, such transgenic animals have their endogenous PAR1 gene replaced with the PAR1 mutant transgene. Transgenic animals (e.g., transgenic mice) expressing a mutant PAR1 gene from a different species (e.g., human) can be generated according to methods well known in the art. For example, techniques routinely used to create and screen for transgenic animals have been described in, e.g., see Bijvoet et al., Hum. Mol. Genet. 7:53-62, 1998; Moreadith et al., J. Mol. Med. 75:208-216, 1997; Tojo et al., Cytotechnology 19:161-165, 1995; Mudgett et al., Methods Mol. Biol. 48:167-184, 1995; Longo et al., Transgenic Res. 6:321-328, 1997; U.S. Pat. Nos. 5,616,491; 5,464,764; 5,631,153; 5,487,992; 5,627,059; 5,272,071; and WO 91/09955, WO 93/09222, WO 96/29411, WO 95/31560, and WO 91/12650. Methods for generating transgenic non-human animals expressing a mutant human gene are also taught in the art, e.g., U.S. Pat. No. 6,284,944.

VI. Screening Methods for Identifying Cytoprotective Agents and Proteases

The novel PAR1-derived cytoprotective peptides and engineered cells or transgenic animals expressing the modified PAR1 receptor can be used to identify additional compounds and proteases with cytoprotective activities. Some embodiments of the invention are directed to identify additional cytoprotective peptides or polypeptides based on the specific PAR1-derived cytoprotective peptides exemplified herein. For example, the TR47 peptide (SEQ ID NO:4) can be used as a scaffold to generate a library of variant or analog peptides and peptidomimetics. The library of candidate agents based on a reference—polypeptide (e.g., TR47 peptide shown in SEQ ID NO:4) can be readily produced using routinely practiced methods as described herein. Such a library of candidate agents can then be screened for optimized or improved cytoprotective activities relative to the activities of the reference polypeptide. The candidate agents can be screened for improvement in any of the cytoprotective activities of the reference polypeptide disclosed herein, e.g., activation of the PI3k-Akt survival pathway or inhibition of staurosporine-induced endothelial cell apoptosis (see Examples below and also Mosnier et al., Biochem J. 373: 65-70, 2003). Variants or analog compounds based on a reference PAR1-derived cytoprotective peptide (e.g., TR47) which are optimized with such a screening method can be employed in the various therapeutic applications described herein.

In some other embodiments, the invention provides screen methods for identifying proteases which can exert cytoprotective activities via signaling through PAR1 (e.g., activating PAR1 via cleavage at the second cleavage site, $Arg^{46}$). Typically, candidate proteases agents are screened for ability to cleavage the mutant PAR1 in vitro at $Arg^{46}$ and/or elicit a cytoprotective cell signaling in vivo. The screening methods can employ the various assays for determining PAR1 cleavage and for monitoring PAR1 mediated cytoprotective signaling, which are exemplified herein and also well known in the art (see Examples below). In some embodiments, the candidate agents can be screened for activity in cleaving a PAR1 N-terminal peptide harboring the $Arg^{46}$ residue (e.g., the peptide of SEQ ID NO:13) via reverse phase HPLC as described in Example 1 below. In some other embodiments, cleavage at $Arg^{46}$ by candidate agents can be examined with a PAR1 cleavage reporter construct which expresses in a host cell (e.g., HEK-293 cells) a labeled PAR1 reporter molecule, e.g., PAR1 with a secreted alkaline phosphatase (SEAP) marker fused to its N-terminus as described in Example 2. Host cells stably expressing the reporter PAR-1 molecule are used to screen for candidate agents that can cleave PAR1 at $Arg^{46}$ and release the detectable SEAP marker.

Alternatively or additionally, the candidate protease agents are screened for ability to activate or promote a cytoprotective signaling activity mediated by PAR1. In these embodiments, an engineered cell (e.g., an endothelial cell) or transgenic non-human animal (e.g., a mouse) which contains a mutation in the PAR1 gene that renders the encoded PAR1 resistant to thrombin cleavage (e.g., human PAR1 with $Arg^{41}Gln$ mutation) is employed. Candidate agents are contacted with the cell or administered to the animal to determine whether they are able to elicit a cytoprotective signaling activity in the cell or the animal. For example, they can be tested for ability to promote phosphorylation of Akt or ERK1/2 in host cells (e.g., EA.hy.926 endothelial cells) as described in Examples 4 and 5 below. Ability of the candidate agent to promote PAR1 cytoprotective signaling can also be assessed by monitoring anti-apoptotic effects in host cells expressing the modified PAR1 gene described herein (e.g., PAR1 with $Arg^{41}Gln$ mutation). Example of such an assay scheme is described in Example 6 below which examined PAR1-derived cytoprotective polypeptides for inhibiting staurosporine-induced endothelial cell apoptosis in EA.hy.926 endothelial cells. An ability to cleave PAR1 at $Arg^{46}$ and/or to elicit a PAR1 mediated cytoprotective signaling activity in cells or animals (e.g., cells expressing a PAR1 $Arg^{41}Gln$ mutant) would indicate that the identified agents are cytoprotective proteases.

For identifying proteases which selectively promote cytoprotective PAR1 signaling, the candidate proteases obtained from the initial screening can be subject to an additional screening step. In this additional step, the candidate agents or proteases are screened for the lack of activity in cleaving the first cleavage site in PAR1 (e.g., $Arg^{41}$ in human PAR1) and/or in activating proinflammatory thrombin signaling. In some methods, this additional screening step is performed with an engineered cell or animal that expresses a mutant PAR1 that is resistant to cleavage at the second cleavage site (e.g., human PAR1 with $Arg^{46}Gln$ mutation). Cleavage of PAR1 at the first cleavage site and activation of proinflammatory thrombin signaling can be monitored with the standard techniques described herein or well known in the art. For example, activation of proinflammatory thrombin signaling can be examined via the routinely practiced assay for phospholipid exposure on platelets and related phospholipid-dependent coagulation assay (see, e.g., Anderson et al., Proc. Natl. Acad. Sci. 96: 11189-93, 1999) or determining the ability of the proteases to stimulate calcium ion fluxes in cells or the ability to phosphorylate ERK1/2 in cells. This additional step allows identification of proteases that are capable of selectively activating the cytoprotective PAR1 signaling but not the thrombin-like proinflammatory PAR1 signaling.

To ensure that the observed cytoprotective signaling is mediated through PAR1, the screening methods can optionally further include a control step by examining the candidate proteases' activity in the presence of a PAR1 inhibitor. For example, small molecule selective antagonists of PAR1 such as SCH 79797 can be used in the screening. SCH79797 and other PAR1 antagonists are well known and readily available to the skilled artisans. See, e.g., Ahn et al., Biochem. Pharmacol. 60: 1425-1434, 2000; Lidington et al., Am. J. Physiol., Cell Physiol. 289: C1437-C1447, 2005; and Damiano et al., Cardiovasc. Drug Rev. 21: 313-26, 2003. As another optional control step, the identified proteases can also be examined for cytoprotective activities in an engineered cell or animal that expresses a mutant PAR1 that is resistant to cleavage at both cleavage sites (e.g., human PAR1 with $Arg^{41}Gln/Arg^{46}Gln$ double mutations). Failure to cleave such a double PAR1 mutant and/or to elicit any cytoprotective signaling response indicates that the observed cytoprotective activities via the $Arg^{41}Gln$ PAR1 mutant is mediated through PAR1.

Other than screening for proteases which activate the cytoprotective PAR1 signaling pathway, the screening methods of the invention can also be employed to identify other types of cytoprotective agonist compounds of PAR1. In these methods, the candidate agents are typically screened for ability in activating PAR1 mediated cytoprotective signaling, e.g., activating the PI3k-Akt survival pathway or inhibition of staurosporine-induced endothelial cell apoptosis as described herein. Similar to the above described screening methods for identifying cytoprotective proteases, cells and/or animals expressing a PAR1 mutant resistant to cleavage at the first cleavage site ($Arg^{41}$) may be employed.

Similarly, PAR1 bearing mutation at the second cleavage site or at both the first and the second cleavage sites may be employed in control screening steps.

To identify proteases with cytoprotective activities, the candidate compounds to be employed in the screening can be any naturally existing or recombinantly produced polypeptides or enzymes (including known proteases). Preferably, the candidate agents or compounds used to screen for novel cytoprotective proteases are proteases, variants or analogs. For example, the candidate agents subject to the screening methods can be, e.g., any serine proteases, metallo proteinases, plasma proteases, cell membrane proteases, cell proteases, engineered proteases, and etc. Many specific examples of proteases from these enzyme classes are all well known in the art and can be readily obtained commercially or recombinantly produced. Other candidate proteases and specific examples of human or mouse proteases suitable for the screening methods of the invention are described in the art, e.g., Overall et al., Nat. Rev. Mol. Cell. Biol. 8:245-57, 2007; Doucet et al., Mol. Aspects Med. 29:339-58, 2008; and Puente et al., Nat. Rev. Genet. 4:544-58, 2003. In some other embodiments, the candidate agents employed for identifying novel cytoprotective proteases can be variants of a known protease. For example, variants or analogs of Activated Protein C (APC), variants of the active forms of prothrombin (active enzyme thrombin), coagulation factor VII (active enzyme factor VIIa), coagulation factor X (active enzyme factor Xa) or variants or matriptase can all be used as candidate agents in the screening methods of the invention. Variants of these proteases can be generated using routinely practiced chemical or biochemical techniques as described herein or well known in the art. For example, APC variants that can be used to screen for novel cytoprotective proteases in the methods of the invention are described in U.S. Patent Application 20100028910.

For identifying PAR1 agonist compounds, the candidate agents to be screened with methods of the invention can be derivative or mimetic compounds of the PAR1 derived cytoprotective polypeptides exemplified herein. For examples, the candidate agents can be polypeptides derived from the polypeptide of SEQ ID NO:2 with various C-terminal truncations (e.g., polypeptides of SEQ ID NOs: 3, 4, and 14-20) or internal deletions. The candidate agents can also be a library of polypeptides derived from the polypeptide of SEQ ID NO:4 which contain one or more amino acid substitutions. Methods for preparing libraries containing diverse populations of peptides, peptoids and peptidomimetics are well known in the art and various libraries are commercially available. See, e.g., Ecker and Crooke, Biotechnology 13:351-360, 1995; and Blondelle et al., Trends Anal. Chem. 14:83-92, 1995; and the references cited therein. See, also, Goodman and Ro, Peptidomimetics for Drug Design, in "Burger's Medicinal Chemistry and Drug Discovery" Vol. 1 (ed. M. E. Wolff; John Wiley & Sons 1995), pages 803-861; and Gordon et al., J. Med. Chem. 37:1385-1401 (1994). One skilled in the art understands that a peptide can be produced in vitro directly or can be expressed from a nucleic acid, which can be produced in vitro. A library of peptide molecules also can be produced, for example, by constructing a cDNA expression library from mRNA collected from a tissue of interest. Methods for producing such libraries are well known in the art (see, for example, Sambrook et. al., Molecular Cloning: A laboratory manual (Cold Spring Harbor Laboratory Press 1989).

Methods of designing peptide derivatives and mimetics and screening of functional peptide mimetics are well known to those skilled in the art. One basic method of designing a molecule which mimics a known protein or peptide is first to identify the active region(s) of the known protein (for example, in the case of an antibody-antigen interaction, one identifies which region(s) of the antibody that permit binding to the antigen), and then searches for a mimetic which emulates the active region. Although the active region of a known polypeptide is relatively small, it is anticipated that a mimetic will be smaller (e.g., in molecular weight) than the protein, and correspondingly easier and cheaper to synthesize and/or have benefits regarding stability or other advantageous pharmacokinetic aspects. Such a mimetic could be used as a convenient substitute for the polypeptide (e.g., SEQ ID NO:4), as an agent for interacting with the target molecule (e.g., PAR1). For example, Reineke et al. (Nat. Biotech. 17; 271-275, 1999) designed a mimic molecule which mimics a binding site of the interleukin-10 protein using a large library of short synthetic peptides, each of which corresponded to a short section of interleukin 10. The binding of each of these peptides to the target (in this case an antibody against interleukin-10) was then tested individually by an assay technique, to identify potentially relevant peptides. Phage display libraries of peptides and alanine scanning methods can be used.

Other methods for designing peptide mimetics to a particular peptide or protein include those described in European Patent EP1206494, the SuperMimic program by Goede et. al., BMC Bioinformatics, 7:11, 2006; and MIMETIC program by Campbell et al., Microbiol. and Immunol. 46:211-215, 2002. The SuperMimic program is designed to identify compounds that mimic parts of a protein, or positions in proteins that are suitable for inserting mimetics. The application provides libraries that contain peptidomimetic building blocks on the one hand and protein structures on the other. The search for promising peptidomimetic linkers for a given peptide is based on the superposition of the peptide with several conformers of the mimetic. New synthetic elements or proteins can be imported and used for searching. The MIMETIC computer program, which generates a series of peptides for interaction with a target peptide sequence, is taught by W. Campbell et. al., 2002. In depth discussion of the topic is reviewed in "*Peptide Mimetic Design with the Aid of Computational Chemistry*" by James R. Damewood Jr. in Reviews in Computational Chemistry, January 2007, Volume 9, Editor(s): Kenny B. Lipkowitz, Donald B. Boyd (John Wiley & Sons, Inc.); and in Tselios, et. al., Amino Acids, 14: 333-341, 1998.

VII. Therapeutic Applications and Pharmaceutical Compositions

The cytoprotective compounds or agents of the invention, including the various PAR1-derived cytoprotective peptides, polypeptides, peptidomimetics, variants or analogs described herein, can be employed in many therapeutic or prophylactic applications by stimulating PAR1 mediated cytoprotective signaling activities. These applications are intended to achieve a desired therapeutic effect such as inhibition of apoptosis or cell death, promotion of cell survival, cytoprotection, neuroprotection, or combinations thereof. In therapeutic applications, a composition comprising a cytoprotective polypeptide or peptidomimetic is to provide cytoprotection to cells at risk for undergoing apoptotic cell death or stress-induced injury either in vivo or in vitro. The composition contains a cytoprotective peptide or peptidomimetic in an amount sufficient to cure, partially arrest, or detectably slow the progression of the cell death or injury. In prophylactic applications, compositions containing a cytoprotective peptide or peptidomimetic are used to prevent apoptotic cell death or injury to a subject who is at the risk of, or has a predisposition, to developing a condition with undesired apoptotic cell death or injury. Such applications allow the subject to enhance the subject's resistance to, or to retard the progression of, the condition.

Typically, the cytoprotective compounds of the invention (e.g., PAR1 polypeptides of SEQ ID NOs: 4-7 and 14-20) are formulated in pharmaceutical compositions for the therapeutic or prophylactic applications disclosed herein. The therapeutic compositions may be administered in vitro to cells in culture, in vivo to cells in the body, or ex vivo to cells outside of a subject, which may then be returned to the body of the same subject or another. The cells may be removed from, transplanted into, or be present in the subject (e.g., genetic modification of endothelial cells in vitro and then returning those cells to brain endothelium).

Subject who are suitable for the therapeutic or prophylactic applications of the present invention are those who could benefit from PAR1 cytoprotective signaling activities. Such subjects include patients at risk for damage to blood vessels or other tissue organs, which damage is caused at least in part by apoptosis. The risk for cell damage may be the result of any one or more of sepsis, ischemia/reperfusion injury, stroke, ischemic stroke, acute myocardial infarction, acute neurodegenerative disease, chronic neurodegenerative disease, organ transplantation, chemotherapy, or radiation injury. These causes of cell damage are not intended in any way to limit the scope of the invention, as one skilled in the art would understand that other diseases or injuries also may put cells at risk for damage caused at least in part by apoptosis. The effective doses or therapeutic doses will be those that are found to be effective at preventing or alleviating cell damage caused at least in part by apoptosis. In some embodiments, the cytoprotective compounds of the invention can be applied to cells or tissue in vitro or in situ. In some other embodiments, the cytoprotective compounds are administered to achieve a desired therapeutic effect in vivo in subjects afflicted with or at risk of developing a condition with associated with undesired cell death or injury. Examples of specific conditions and desired therapeutic effects include the following: reduction of mortality in sepsis (e.g., adult severe sepsis); reduction of death in pediatric meningococcemia; promotion of diabetic ulcer wound healing; treat or prevent injuries in ischemic stroke, neurotrauma, and other acute or chronic neurodegenerative conditions; treat or prevent injuries in cardiac ischemia/reperfusion, hepatic ischemia/reperfusion, renal ischemia/reperfusion; treat or prevent inflammatory lung injury, gastrointestinal injury; treat or prevent flap necrosis in reconstructive surgery; prolong survival following Ebola infection; and reduce damage to a subject caused by radiation.

Pharmaceutical compositions of the invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. The pharmaceutical compositions of the invention may be administered by any known route. By way of example, the composition may be administered by a mucosal, pulmonary, topical, or other localized or systemic route (e.g., enteral and parenteral). In particular, achieving an effective amount of the cytoprotective compound in the central nervous system may be desired. This may involve a depot injection into or surgical implant within the brain. "Parenteral" includes subcutaneous, intradermal, intramuscular, intravenous, intra-arterial, intrathecal, and other injection or infusion techniques, without limitation.

Suitable choices in amounts and timing of doses, formulation, and routes of administration can be made with the goals of achieving a favorable response in the subject (i.e., efficacy or therapeutic), and avoiding undue toxicity or other harm thereto (i.e., safety). Administration may be by bolus or by continuous infusion. Bolus refers to administration of a drug (e.g., by injection) in a defined quantity (called a bolus) over a period of time. Continuous infusion refers to continuing substantially uninterrupted the introduction of a solution into a blood vessel for a specified period of time. A bolus of the formulation administered only once to a subject is a convenient dosing schedule, although in the case of achieving an effective concentration of the cytoprotective compound in the brain more frequent administration may be required. Treatment may involve a continuous infusion (e.g., for 3 hr after stroke) or a slow infusion (e.g., for 24 hr to 72 hr when given within 6 hr of stroke). Alternatively, it may be administered every other day, once a week, or once a month. Dosage levels of active ingredients in a pharmaceutical composition can also be varied so as to achieve a transient or sustained concentration of the compound or derivative thereof in a subject and to result in the desired therapeutic response.

The pharmaceutical compositions of the invention may be administered as a formulation, which is adapted for direct application to the central nervous system, or suitable for passage through the gut or blood circulation. Alternatively, pharmaceutical compositions may be added to the culture medium. In addition to active compound, such compositions may contain pharmaceutically acceptable carriers and other ingredients known to facilitate administration and/or enhance uptake. It may be administered in a single dose or in multiple doses, which are administered at different times. A unit dose of the composition is an amount of the cytoprotective compounds which provides effective cytoprotection, inhibits apoptosis or cell death, and/or promotes cell survival. Measurement of such values can be performed with standard techniques well known in the art, e.g., clinical laboratories routinely determine these values with standard assays and hematologists classify them as normal or abnormal depending on the situation.

When administered to a subject in vivo, the pharmaceutical compositions typically contain a therapeutically effective amount of the active cytoprotective compound. A therapeutically effective amount is the total amount of the cytoprotective compound that achieves the desired cytoprotective effect. Depending on the species of the subject or disease to be treated, the therapeutic amount may be about 0.01 mg/kg/hr to about 1.1 mg/kg/hr if administered by continuous infusion over 4 hour to 96 hour, to as little as about 0.01 mg/kg/hr to about 0.10 mg/kg/hr for about 24 hours. Preferably, the therapeutic dose would be administered by continuous infusion for about 4 to about 72 hours. More preferably, by continuous infusion for about 4 to about 48 hours. More preferably, by continuous infusion for about 12 to about 48 hours. More preferably, by continuous infusion for about 12 to about 36 hours. More preferably, by continuous infusion for about 4 to about 36 hours. More preferably, by continuous infusion for about 12 to about 24 hours. Most preferably, by continuous infusion for about 24 hours. In other examples, a therapeutically effective amount for bolus administration can typically be 2 mg/kg or less, 1 mg/kg or less, 0.5 mg/kg or less, 0.04 mg/kg or less, 0.03 mg/kg or less, 0.02 mg/kg or less, 0.01 mg/kg or less, or 0.005 mg/kg or less. Typically, the therapeutic amount may be based on titering to a blood level amount of the cytoprotective compound of about 0.01 µg/ml to about 1.6 µg/ml, preferably from about 0.01 µg/ml to about 0.5 µg/ml. It is also within the skill of the art to start doses at levels lower than required to achieve the desired therapeutic effect and to gradually increase the dosage until the desired effect is achieved. It is likewise within the skill of the art to determine optimal concentrations of variants to achieve the desired effects in the in vitro and ex vivo preparations of the invention. Depending on initial assay results, optimal concentrations can be in the range of, e.g., about 1-1,000 nM or about 1-200 µM depending on the general nature of the compound.

EXAMPLES

The following examples are provided to further illustrate the invention but not to limit its scope. Other variants of the invention will be readily apparent to one of ordinary skill in the art and are encompassed by the appended claims.

Example 1: Activated Protein C Cleaves a Synthetic PAR1 Peptide (TR33-62) at $Arg^{46}$

| Peptide name | Peptide sequence |
|---|---|
| TFLL (TR42-51 with S42T) | TFLLRNPNDK (SEQ ID NO: 8) |
| NPND (TR47-66) | NPNDKYEPFWEDEEKNESGL (SEQ ID NO: 4) |
| scr-NPND (scrambled TR47-66) | GDENENEKPNWYELKEPDSF (SEQ ID NO: 9) |
| TR24-41 | TRARRPESKATNATLDPR (SEQ ID NO: 10) |
| TR24-46 | TRARRPESKATNATLDPRSFLLR (SEQ ID NO: 11) |
| TR42-66 | SFLLRNPNDKYEPFWEDEEKNESGL (SEQ ID NO: 12) |
| TR33-62 | ATNATLDPRSFLLRNPNDKYEPFWEDEEKN (SEQ ID NO: 13) |

Figure 2:
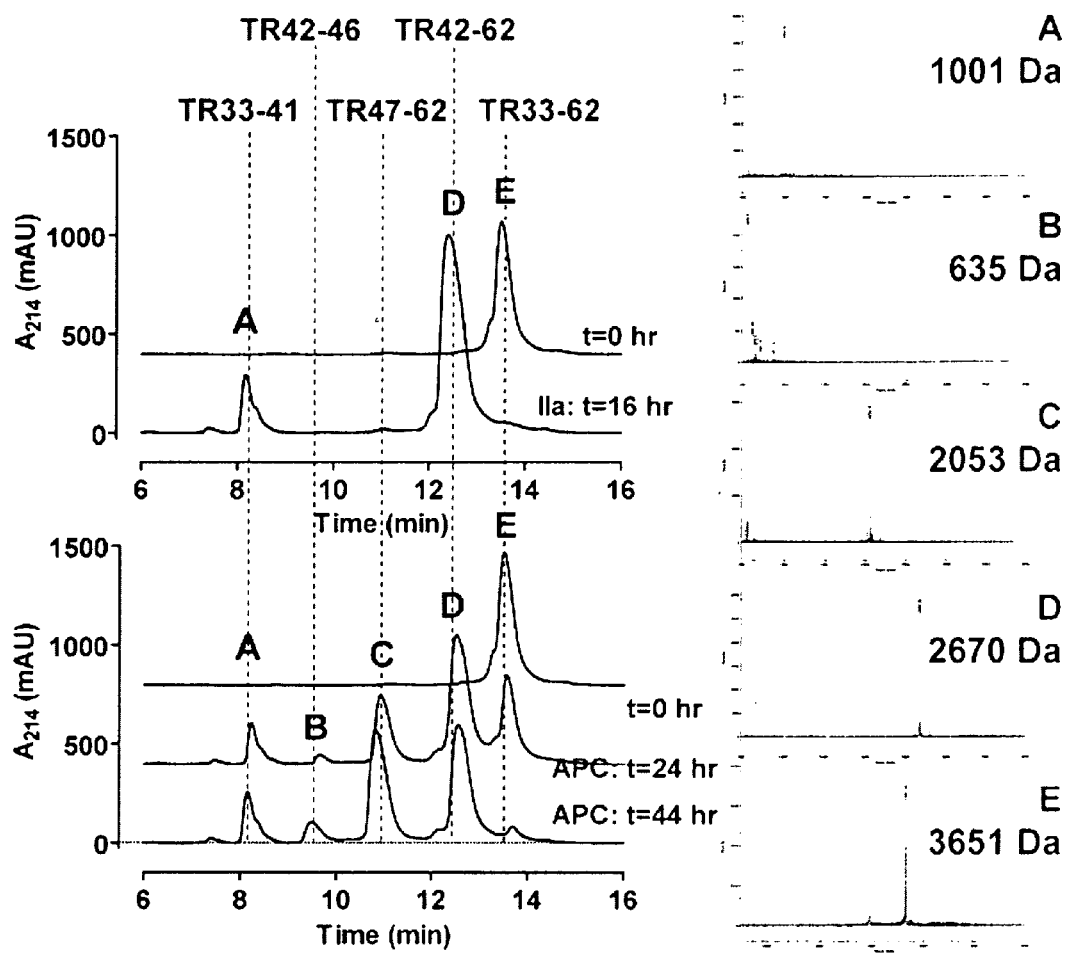
FIG. 2 shows that Activated Protein C cleaves a synthetic PAR1 peptide (TR33-62) at $Arg^{46}$.

To characterize APC cleavage sites in PAR1 N-terminal tail, we studied the HPLC patterns from cleavage of a synthetic peptide ("TR33-62") comprising residues 33-62 of the PAR1 N-terminus by thrombin and APC and got the mass spec values for each observed peak. The results are shown in FIG. 2. In the HPLC profiles, the uncleaved substrate TR33-62 (peak E) gave the correct mass of 3,651 and the two fragments produced by thrombin (peaks A and D) corresponded to masses of 1,001 and 2,670 for cleavage at $Arg^{41}$ as expected. In contrast to thrombin, APC gave four cleavage peaks (A and D, plus B and C) which corresponded to masses for cleavages at both $Arg^{41}$ (peaks A and D) and at Arg46 (peaks B and C). Thus, APC cleaves this PAR1 peptide at $Arg^{46}$ as well as at $Arg^{41}$.

Methods: Cleavage by APC or thrombin of a synthetic ("TR33-62") PAR1 peptide (Biosynthesis) comprising residues 33-62 of the PAR1 N-terminus (SEQ ID NO:13) was analyzed by reverse phase HPLC on a C18 column with absorbance monitoring at 214 nm. APC (500 nM) or thrombin (5 nM) were incubated with TR33-62 (100 in Hepes (20 mM) buffered saline (147 mM NaCl/4 mM KCl) pH 7.4 (HBS) for various times after which 20 µl of 1.2 M perchloric acid was added to stop the reaction. Samples were subjected to reverse phase HPLC on a C18 column while the eluent was monitored at 214 nm during a 0%-67% gradient of acetonitrile in water containing 0.1% trifluoroacetic acid. Peptide fragments were collected and subjected to MALDI-TOF (Scripps mass spectrometry core facility) analysis.

Figure 3:
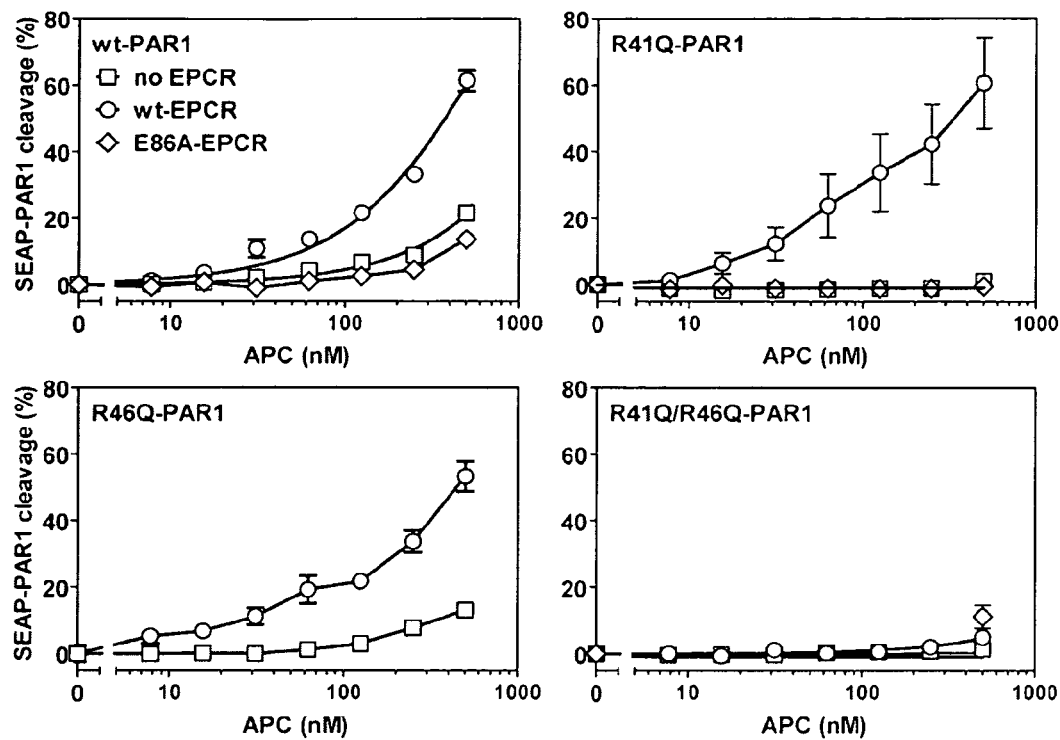
FIG. 3 shows that Activated Protein C cleaves PAR1 at $Arg^{46}$ on transfected HEK-293 cells.

Example 2: Activated Protein C (APC) Cleaves PAR1 at $Arg^{46}$ on Transfected HEK-293 Cells To facilitate analysis of APC-mediated PAR-1 activation, we created a full-length PAR-1 construct linked at the N-terminus to an alkaline phosphatase reporter group (SEAP). Selection of stable cell lines expressing both endothelial protein C receptor (EPCR) (wt or E86A) and SEAP-PAR1 allowed for a reliable and reproducible analysis of EPCR-dependent PAR-1 activation by APC. The results are shown in FIG. 3. Mass-spec analysis of cleavage fragments generated by APC of a synthetic PAR-1 N-terminal tail peptide (TR33-62) identified both $Arg^{41}$ and $Arg^{46}$ as potential cleavage sites for APC proteolysis, as noted above. To characterize the cleavage of PAR1 by APC on cells, SEAP-PAR1 mutants were generated with either the thrombin cleavage site $Arg^{41}$ mutated (R4Q-SEAP-PAR1) or the APC cleavage site $Arg^{46}$ mutated (R46AQ-SEAP-PAR1). R41Q-SEAP-PAR1 was cleaved by APC in the presence of EPCR. This surprising result was also obtained for R41A-SEAP-PAR1. Mutagenesis of R46Q in SEAP-PAR1 did not eliminate PAR1 cleavage by APC whereas mutagenesis of both R41Q/R46Q in SEAP-PAR1 eliminated PAR-1 cleavage by APC. Interestingly, APC did not cleave R41A-SEAP-PAR1 in the absence of EPCR whereas it did cleave wt-SEAP-PAR1 and R46Q-SEAP-PAR1, suggesting that in the absence of EPCR, APC can still cleave PAR-1 at $Arg^{41}$ but not at $Arg^{46}$.

These data identified PAR-1 residue $Arg^{46}$ as an alternative to $Arg^{41}$ for proteolysis of intact PAR1 on cell surfaces by APC. Thrombin did not show any cleavage of R41Q-PAR1, i.e., it did not cleave PAR1 on cells at $Arg^{46}$. The relatively nonspecific protease, elastase, cleaved all PAR1 constructs on cells with similar efficacy, independent of EPCR. A similar set of PAR1 constructs where Ala replaced $Arg^{41}$ and/or $Arg^{46}$ showed essentially identical results. We conclude that EPCR-dependent PAR-1 cleavage at $Arg^{46}$ by APC could result in cytoprotective signaling whereas PAR-1 cleavage at $Arg^{41}$ by thrombin results in proinflammatory PAR-1 signaling.

Methods: A PAR-1 cleavage reporter construct was made in which a secreted alkaline phosphatase (SEAP) was fused to the N-terminus of PAR-1 which is released by proteolysis by APC or thrombin at residue $Arg^{41}$ or $Arg^{46}$ as described in Mosnier et al., Blood. 2009; 113:5970-5978. SEAP-PAR1, either in the presence or absence of wt-EPCR, were transfected into HEK-293 cells to obtain stable cells expressing SEAP-PAR1 or wt-EPCR/SEAP-PAR1. Mutations in SEAP-PAR1 were introduced using the Quick-change method (Agilent). Cells were grown in 96-wells plates to confluency in Dulbeco's modified Eagle media (DMEM): Ham's F-12 (Invitrogen) supplemented with penicillin-streptomycin-glutamine (PSG) (Gibco) and 10% fetal bovine serum (Omega) in a humidified atmosphere at 37° C. and 5% $CO_2$. Cells were washed with Hank's balanced salt solution (HBSS; Invitrogen) supplemented with 1.3 mM $CaCl_2$, 0.6 mM $MgCl_2$ and 0.1% endotoxin free BSA (Calbiochem) and incubated with APC. After 60 min, SEAP release was determined using 1-step PNPP (Pierce). Values were corrected for background activity derived from the same cells incubated in the absence of APC and expressed as a percentage of total SEAP available on the cell membrane.

Example 3: Activated Protein C Cleaves PAR1 at $Arg^{46}$ on EA.hy.926 Endothelial Cells We showed above that Activated Protein C (APC) cleaves a synthetic PAR1 N-terminal tail peptide at Are and $Arg^{46}$. On HEK293 cells APC cleaved a SEAP-PAR1 fusion construct at $Arg^{41}$ and $Arg^{46}$ when cells were co-transfected with wt-EPCR. To determine whether APC cleaves endogenous PAR1 at the non-canonical $Arg^{46}$ site on endothelial cells in the presence of endogenous endothelial protein C receptor (EPCR), anti-PAR1 antibodies with defined epitopes were used to characterize the presence or disappearance of specific PAR1 epitopes on the cell surface of EA.hy.926 endothelial cells upon incubation with thrombin or APC. Specifically, PAR1 peptides (Biosynthesis) were synthesized and purified to >95%. Peptides were coated to 96-well maxisorp plates (Nunc) at 10 μM in carbonate buffer pH 9.0. Plates were blocked with Tris (50 mM) buffered saline (150 mM NaCl) pH 7.4 (TBS) containing 3% BSA. Subsequently, antibodies were incubated at 2 μg/ml in blocking buffer. After washing with TBS/0.1% Tween appropriate HRP-labeled secondary antibodies (DAKO) were added at 1:1000 dilution in blocking buffer. Plates were then washed with TBS/0.1% Tween and developed with o-phenylenediamine dihydrochloride (OPD) for the appropriate time, reactions were stopped by addition of ⅓ volume 1M $H_2SO_4$ and absorbance was determined at 490 nm.

Figure 4:
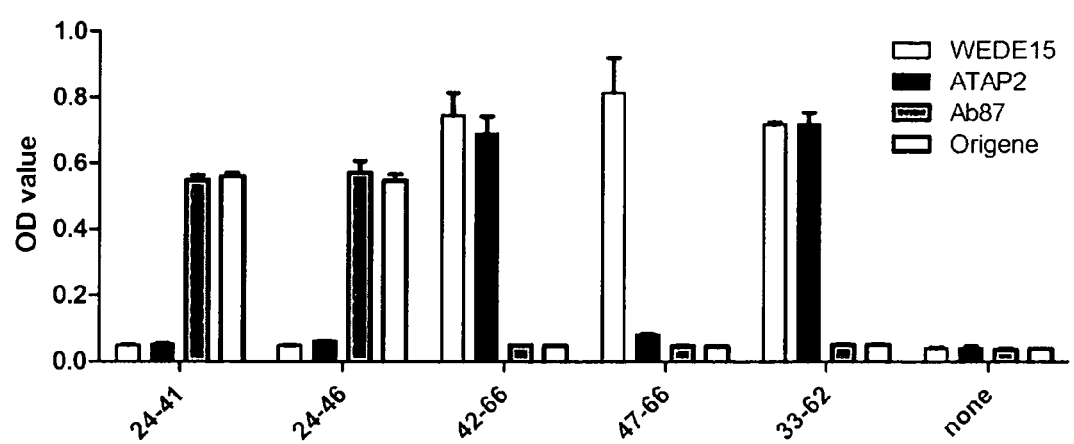
FIG. 4 shows that Activated Protein C cleaves PAR1 at $Arg^{46}$ on EA.hy.926 endothelial cells.

The results obtained from the study are shown in FIG. 4. First, the epitopes of various PAR1 antibodies were validated using solid-phase binding assay with immobilized PAR1 peptides. Goat anti-PAR1 antibodies (Ab87 and Origene), raised against the PAR1 peptide residues 1-100 and residues 24-37 respectively, reacted only with PAR1 peptides TR24-41 and TR24-46 but not with PAR1 peptides TR42-66 and TR47-66. Also, these goat anti-PAR1 antibodies did not react with PAR1 peptide 33-62 indicating that the epitope of these antibodies requires the PAR1 sequence 24-32 which must represent most or all of the epitope for these antibodies. Thus, these antibodies are cleavage sensitive antibodies and their signals on cells are anticipated to diminish when APC or thrombin cleaves PAR1 to liberate soluble activation peptides (e.g., residues 24-41, 24-46, and 42-46) regardless of whether that cleavage occurs at $Arg^{41}$ or at $Arg^{46}$. Monoclonal anti-PAR1 antibody ATAP2 has an epitope confined within residues 41-55 of PAR1 (Brass et al., J Biol Chem. 1994; 269:2943-2952).

In a solid-phase binding assay with immobilized PAR1 peptides ATAP2 did not react with the N-terminal cleavage products TR24-41 or TR24-46. In contrast, ATAP2 did bind to PAR1 peptide TR42-66 but not to the shorter peptide TR47-66 indicating that critical for epitope recognition are residues within the PAR1 sequence 42-46. Thus, ATAP2 is a cleavage site sensitive antibody. Its signal on cells is anticipated to diminish when APC cleaves PAR1 at $Arg^{46}$ but not when PAR1 is cleaved at $Arg^{41}$, therefore in the absence of a signal for the goat anti-PAR1 antibodies (ab87 or Origene) which reports cleavage of the PAR1 N-terminal tail, the presence or absence of the ATAP2 signal on cells will report whether PAR1 is cleaved at $Arg^{41}$ or at $Arg^{46}$, respectively. Monoclonal anti-PAR1 antibody WEDE15 has an epitope confined within residues 51-64 of PAR1 (Brass et al., J. Biol. Chem. 269:2943-2952, 1994). In a solid-phase binding assay with immobilized PAR1 peptides WEDE15 did not react with the N-terminal cleavage products TR24-41 or TR24-46. WEDE15 did bind to PAR1 peptides TR42-66, TR47-66 and TR33-62 confirming that the critical epitope residues reside within the PAR1 sequence 47-62. Thus, WEDE15 binding to PAR1 is insensitive to cleavage at $Arg^{46}$ by APC. The WEDE15 binding signal on cells is anticipated to remain unchanged upon APC or thrombin cleavage of PAR1, regardless of whether that cleavage occurs at $Arg^{41}$ or at $Arg^{46}$. Therefore, WEDE15 will report the total of available PAR1 molecules on the surface of the cell membrane and can be used for normalization of the signals for the goat anti-PAR1 antibodies (ab87 or Origene) and ATAP2 whose epitopes are sensitive to proteolysis of PAR1.

Subsequently, these antibodies were used in an on cell Western (OCW) immunoassay on EA.hy.926 endothelial cells to determine whether APC cleaves PAR1 at $Arg^{46}$ in the presence of endogenous PAR1 and EPCR expression. In this study, confluent EA.hy.926 cells plated in black clear bottom 96-well tissue culture treated plates were incubated for 1 hr with 0.5 nM thrombin or 25 nM APC. Incubations were performed at 4° C. to minimize receptor recycling and internalization. After fixation and staining, antibody signals were normalized for total cell number using the cell permeable nuclear dye Draq5 and antibody signals for the goat anti-PAR1 antibodies (Ab87 and Origene) and ATAP2 were expressed as a fraction of the signal obtained for WEDE15 reflecting the total PAR1 present on the cell surface.

Figure 5:
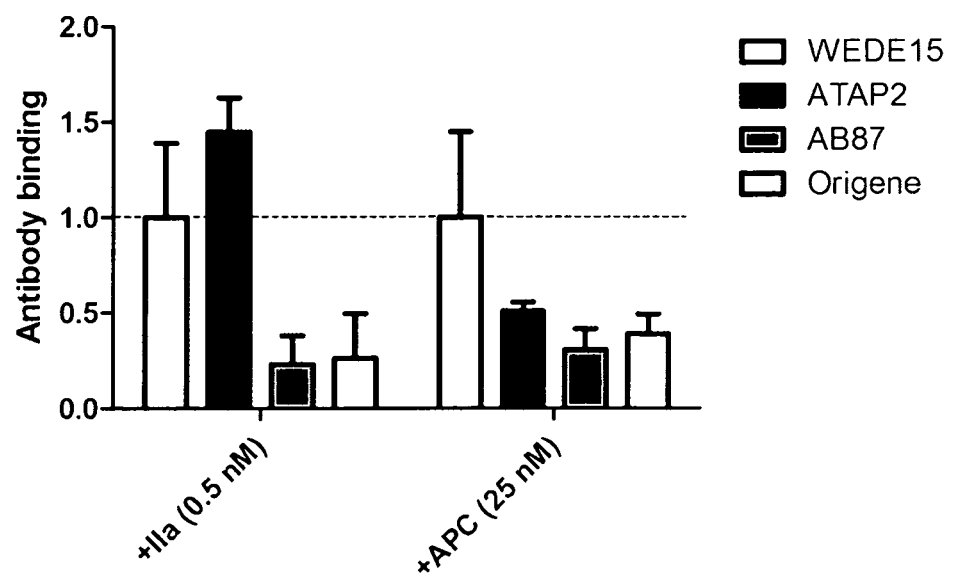
FIG. 5 shows that APC cleaves PAR1 at $Arg^{46}$ on untransfected EA.hy.926 endothelial cells expressing endogenous EPCR and PAR1.

Results obtained from this study are shown in FIG. 5. Incubation of the EA.hy.926 endothelial cells with thrombin or APC resulted in 60-75% reduction of the cleavage sensitive goat anti-PAR1 antibody (Ab87 and Origene) signals indicating that both thrombin and APC cleaved PAR1. The signal for ATAP2 was not significantly different for that of WEDE15 upon incubation of the cells with thrombin indicating that thrombin had cleaved PAR1 at the canonical $Arg^{41}$ cleavage site. In contrast, the ATAP2 signal decreased 50% compared to WEDE15 upon incubation of the cells with APC indicating that significant APC-mediated cleavage of PAR1 at the non-canonical cleavage site at $Arg^{46}$ had occurred.

Thus, on untransfected EA.hy.926 endothelial cells expressing endogenous EPCR and PAR1, APC cleaves PAR1 at $Arg^{46}$ whereas thrombin cleaves PAR1 at $Arg^{41}$ giving rise to different new N-termini starting at $Ser^{42}$ after thrombin cleavage or starting at $Asn^{47}$ after APC cleavage. Because the new N-terminus acts as a tethered ligand (agonist) for activation of the PAR1 receptor and induction of signaling pathways, this difference in new N-terminal residues, i.e., SFLLRN (SEQ ID NO:21)-etc. for thrombin versus NPNDKY (SEQ ID NO:14)-etc. for APC, shows that thrombin and APC create different tethered-ligands (agonists). Different receptor agonists are known to be able to activate G protein-coupled receptors (GPCR) differently, resulting in the induction of different cell signaling pathways. It was therefore conceivable that, because APC and thrombin create different PAR1 agonists, APC and thrombin activate PAR1 differently to such an extent that different cell signaling pathways could be activated, depending on whether the PAR1 agonist is derived from a N-terminus that starts with SEQ ID NO:21 or one that starts with SEQ ID NO:14.

Detailed methods and steps used for the study shown in FIG. 5 are as follows: EA.hy.926 cells (ATCC: CRL-2922) were grown in black clear bottom 96 well plates (Nunc) in DMEM (Invitrogen #12430) supplemented with glutamax (Invitrogen #35050) and 10% FBS (Hyclone #35-011-CV) in a 37° C. cell incubator with a humidified atmosphere and 5% $CO_2$ in air until confluency. Cells were prechilled to 4° C. and treated for 1 hr with thrombin (0.5 nM) or APC (25 nM) in Hanks buffered salt solution (HBSS; Invitrogen) supplemented with 0.1% endotoxin free BSA (Calbiochem) 1.3 mM $CaCl_2$ and 0.6 mM $MgCl_2$. Subsequently cells were fixed with methanol free 4% para-formaldehyde (Pierce), washed with phosphate buffered saline (PBS; Invitrogen) and blocked with Odyssey blocking buffer (Licor). Cells were incubated with 2.5 µg/ml goat anti-PAR1 antibodies ab86 (Abcam #ab66068) or Origene (Origene #TA305911) or with 10 µg/ml ATAP2 or WEDE15 in Odyssey blocking buffer. After washing with PBS/0.1% Tween (1/600) IRDye 800CW-labelled secondary goat anti-mouse or donkey anti-goat antibodies (Licor) were added to the cells in Odyssey blocking buffer and 1/10,000 Draq5 (Biostatus) for cell normalization. After final washing with PBS/0.1% Tween, IR fluorescence of bound antibodies was determined using the Odyssey (Licor). Background fluorescence was determined by omitting the primary antibody and subtracting background values from all observed values.

Example 4: Activation of Cell Signaling (ERK 1/2) by APC, Thrombin and TR42-51 (TRAP; TFLL) and TR47-66 (NPND) Peptides on EA.hy.926 Endothelial Cells To assess whether PAR1 cleaved at $Arg^{46}$ would generate a PAR1 N-terminus that is capable of promoting PAR1 signaling, we studied the effects of synthetic peptides on ERK1/2 phosphorylation in EAhy926 endothelial cells. ERK1/2 phosphorylation is an established marker of PAR1-dependent signaling by thrombin and APC on endothelial cells (Riewald et al., Science. 2002; 296:1880-1882). The peptides included a Thrombin Receptor Activating Peptide ("TRAP"; aka "TFLL") reflecting the sequence of PAR1 residues 42-51 (SEQ ID NO:8), a peptide comprising residues 47-66 (TR47-66) that would be generated by APC cleavage at $Arg^{46}$ (SEQ ID NO:4), and a control scrambled TR47-66 peptide (designated "scr-TR47-66") containing scrambled residues 47-66 (SEQ ID NO:9). Relative phosphorylation of ERK1/2 was determined using the LI-COR Odyssey infrared imaging system which permits quantitative analysis over a wide dynamic range.

Figure 6:
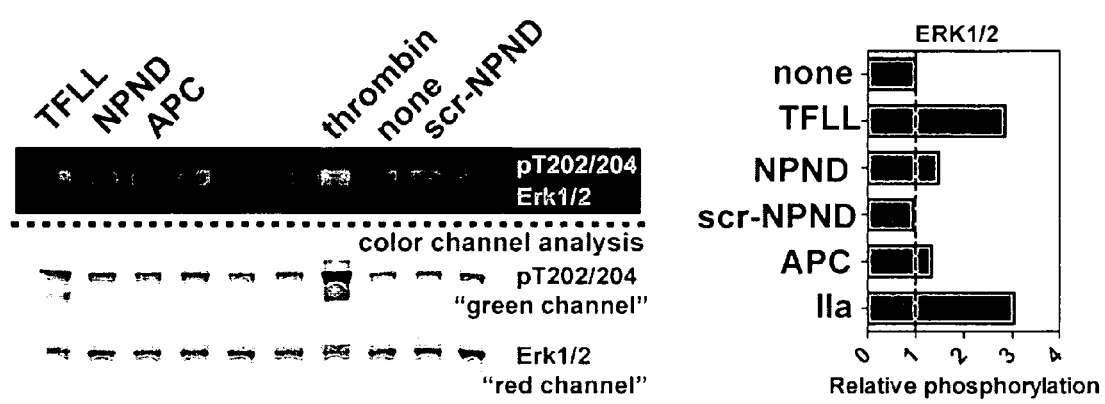
FIG. 6 shows activation of cell signaling (ERK 1/2) by APC, thrombin and TR42-51 peptide (SEQ ID NO:8) and cytoprotective TR47-66 peptide (SEQ ID NO:4) on EA.hy.926 endothelial cells.

As shown in FIG. 6, the Li-COR Odyssey permits simultaneous detection of multiple signals when detecting antibodies yield either red or green signals; notably each color for different antibodies for overlapping bands can be deconvoluted from the total signal. In this figure (left), anti-pT202Y204-ERK1/2 antibodies appear green while total anti-ERK1/2 antibodies appear red, and orange intensity reflects overlaps. Cells were treated for 5 min with 10 nM APC or thrombin or 10 µM TFLL peptide or 50 µM TR47-66 or scr-TR47-66 prior to cell lysis and immunoblotting analysis. The signal for phosphorylated ERK1/2 (green channel) was normalized to the signal for total ERK1/2 antigen (red channel) to quantify relative phosphorylation as a ratio, and the results are seen in the bar graph. Data in the bar graph show that thrombin and TRAP caused a 3-fold increase in ERK1/2 phosphorylation and that APC and TR47-66 caused a 1.5-fold increase in phosphorylation. The control scr-TR47-66 peptide (scrambled residues 47-66) caused no increase. Thus, these data suggest that the amino acid sequence of PAR1 that has been cleaved at $Arg^{46}$ can cause signaling, i.e. ERK1/2 phosphorylation, that is typical of PAR1-dependent signaling initiated by APC or thrombin.

These data indicate that APC can initiate signaling by cleavage at $Arg^{46}$ in PAR1.

Methods: EA.hy.926 cells (ATCC: CRL-2922) were grown in 6-well plates in DMEM (Invitrogen #12430) supplemented with glutamax (Invitrogen #35050) and 10% FBS (Hyclone #35-011-CV) in a 37° C. cell incubator with a humidified atmosphere and 5% $CO_2$ in air until confluency. Cells were serum starved overnight and treated for 5 min with PAR1 peptides TFLL (10 µM), NPND (250 µM) or scr-NPND (250 µM) or with vehicle control thrombin or APC in thrombin (10 nM) or APC (10 nM) in serum free media. Subsequently cells were resuspended in lysis buffer with protein and phosphatase inhibitors, cell lysates were applied to SDS-PAGE gel electrophoresis on 10% Bis-Tris gels with MOPS running buffer (Invitrogen) and transferred to PVDF membrane (Millipore) for Western blot analysis. Blots were blocked in Odyssey blocking buffer (Licor) and incubated with a combination of mouse anti-ERK1/2 (1/2000; Cell Signaling #3A7) and rabbit anti-pT202/204 ERK1/2 (1/1000; cell signaling #D13.14.4E) antibodies in Odyssey blocking buffer (Licor). After washing, blots were incubated with IRDye680-labeled donkey anti-mouse (1/10,000; Licor) and IRDye800CW-labeled donkey anti-rabbit (1/10,000), washed again with PBS/0.1% Tween and IR fluorescence of bound antibodies was determined using the Odyssey (Licor).

Example 5: Preferential Activation of Akt by the TR47-66 Peptide Versus Preferential Activation of ERK1/2 by the TR42-51 Peptide (TFLL) on EA.hy.926 Endothelial Cells Activated Protein C (APC) cleaves a synthetic PAR1 tail peptide at $Arg^{41}$ and $Arg^{46}$; furthermore, APC cleaves SEAP-PAR1 mutants with the mutations R41A or R41Q but not SEAP-PAR1 with both R41Q/R46Q mutations. Thrombin does not cleave PAR1 at $Arg^{46}$. It was thus hypothesized that a new PAR1 N-terminus beginning at residue Asn-47 promotes PAR1 signaling and APC cytoprotective activities. Since phosphorylation of signaling network components is useful for monitoring activation of signaling pathways, the effects of synthetic PAR1 peptides on Akt and ERK1/2 phosphorylation in EA.hy.926 human endothelial cells were studied. Cells were treated for 0, 5 or 30 min with peptides prior to cell fixation, permeabilization of cells and subsequent immunoblotting analysis ("in-cell Western blotting"). Relative phosphorylation of Akt at $Ser^{473}$ ($pSer^{473}$-Akt) or of ERK1/2 at Thr202/204 (pERK1/2) in endothelial cells was quantified using the LI-COR Odyssey infrared (IR) fluorescence imaging system which permits "in cell" Western blots. The Odyssey permits simultaneous quantification of different antibodies that yield either red or green signals.

Figure 7:
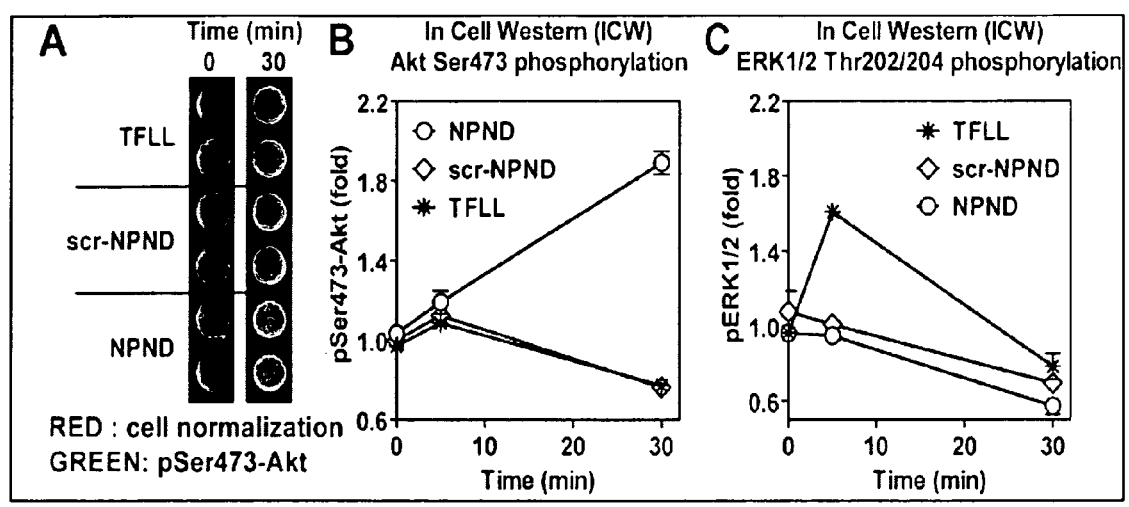
FIG. 7 shows preferential activation of Akt by the TR47-66 peptide (SEQ ID NO:4) versus preferential activation of ERK1/2 by the TR42-51 peptide (SEQ ID NO:8) on EA.hy.926 endothelial cells.

Results obtained from the study are shown in FIG. 7. As seen from the figure (panel A), a cell marker (red intensity) can be used to quantify relative numbers of cells in each well, permitting a very accurate normalized ratio calculation of the relative phosphorylation of Akt (green intensity for $pSer^{473}$-Akt in panel A) or similarly of ERK1/2 (data not shown). The peptides studied included: 1) "TRAP" (Thrombin Receptor Activating Peptide) ("TFLL") that represents PAR1 residues (42-TFLLRNPNDK-51, with Tin place of S42; see Vu et al., Cell. 1991; 64:1057-1068) (SEQ ID NO:8); 2) "NPND" designating PAR1 residues 47-NPND-KYEPFWEDEEKNESGL-66 (SEQ ID NO:4) comparable to the new N-terminal sequence appearing after cleavage of PAR1 at $Arg^{46}$ by APC; and 3) "scr-NPND", a negative control for NPND containing scrambled PAR1 residues 47-66 (SEQ ID NO:9). The NPND peptide, comprising PAR1 residues 47-66, caused a time-dependent sustained increase in pSer$^{473}$-Akt compared to TFLL and scr-NPND peptides which had essentially no effect on Akt phosphorylation (panel B). In contrast, the TRAP compound, TFLL comprising PAR1 residues 42-51, quickly but transiently stimulated ERK1/2 phosphorylation, compared to NPND and scr-NPND which had essentially no effect on ERK1/2 phosphorylation (panel C). These data indicate that cleavage at Arg$^{41}$ by thrombin or APC generates a new N-terminus which is a classical TRAP whereas APC's cleavage at Arg$^{46}$ generates a new N-terminus beginning with NPND which can initiate novel signaling that causes phosphorylation of Akt, but not of ERK1/2. Activation of the Akt-survival pathway is known to provide cytoprotective activities that enable cells to survive potentially lethal stimuli (e.g., hypoxia, radiation, oxidative stress, etc.).

Methods: EA.hy.926 cells (ATCC: CRL-2922) were grown in black clear bottom 96 well plates (Nunc) in DMEM (Invitrogen #12430) supplemented with glutamax (Invitrogen #35050) and 10% FBS (Hyclone #35-011-CV) in a 37° C. cell incubator with a humidified atmosphere and 5% $CO_2$ in air until confluency. Cells were treated for 0, 5 or 30 min with PAR1 peptides TFLL (50 µM), NPND (250 µM) or scr-NPND (250 µM) or with vehicle in serum free media. Subsequently cells were fixed with methanol free 4% para-formaldehyde (Pierce), washed with phosphate buffered saline (PBS; Invitrogen) containing 1% triton X-100 and blocked with Odyssey blocking buffer (Licor). Cells were incubated with rabbit anti-pT202/Y204 ERK1/2 (1/1000; Cell signaling D13.14.4E) or rabbit anti-pSer$^{473}$ (1/100; cell signaling D9E) with Odyssey blocking buffer. After washing with PBS/0.1% Tween (1/800), IRDye 800CW-labelled secondary goat anti-rabbit antibodies (Licor) were added to the cells in Odyssey blocking buffer and 1/10,000 Draq5 (Biostatus) for cell normalization. After final washing with PBS/0.1% Tween IR, the fluorescence of bound antibodies was determined using the Odyssey (Licor). Background fluorescence was determined by omitting the primary antibody and subtracting values for controls from all other observed values.

Figure 8:
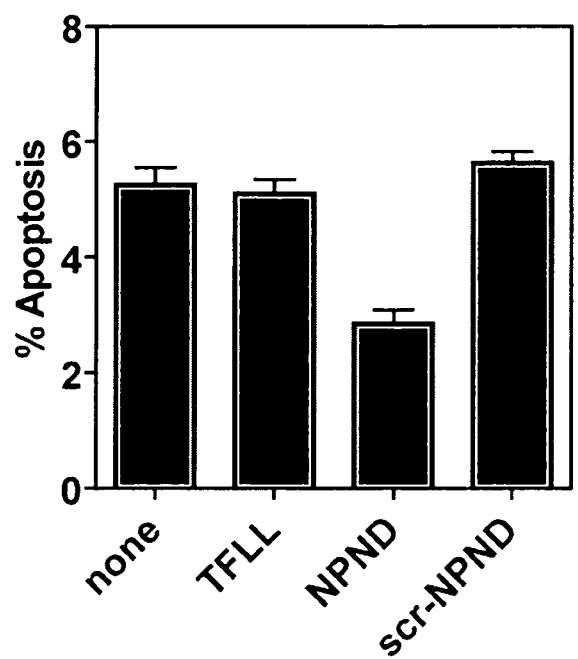
FIG. 8 shows that PAR1 derived cytoprotective polypeptide TR47-66 (SEQ ID NO:4) conveys anti-apoptotic effects on EA.hy.926 endothelial cells.

Example 6: TR47-66 Peptide Conveys Anti-Apoptotic Effects on EA.hy.926 Endothelial Cells Activated Protein C (APC) conveys anti-apoptotic activity to EA.hy.926 cells that requires functional PAR1 receptor and APC binding to the endothelial protein C receptor (EPCR). See, e.g., Mosnier et al., Biochem J. 2003; 373: 65-70; and Mosnier et al., Blood. 2007; 109:3161-3172. To determine whether APC's anti-apoptotic activity is the result of PAR1 cleavage at Arg$^{41}$ or at Arg$^{46}$, PAR1 peptides representing the newly generated N-termini after cleavage at Arg$^{41}$ (TFLL) or at Arg$^{46}$ (NPND) were evaluated for their ability to inhibit staurosporine-induced endothelial cell apoptosis. It was found that the NPND peptide significantly inhibited endothelial cell apoptosis (FIG. 8). This demonstrates that non-canonical cleavage of PAR1 at Arg$^{46}$ generates a new, signaling competent N-terminus that conveys anti-apoptotic activity. In contrast, the TFLL peptide representing the new N-terminus of PAR1 resulting from canonical cleavage of PAR1 at Arg$^{41}$ and the control scrambled sequence scr-NPND peptide did not convey detectable anti-apoptotic effects (FIG. 8).

To further confirm activation of Akt by the TR47-66 peptide, Akt-mediated inactivation of glycogen synthase kinase 3β (GSK3β) via phosphorylation at Ser9 was determined. GSK3β is a well-known downstream substrate for Akt. It was found that TR47-66 induced significant Ser9-GSK3β phosphorylation starting at 30 min with a time-course that fell well within the time course of TR47-mediated Akt activation. Similar to phosphorylation of Akt at Ser473, no phosphorylation of GSK3β at Ser9 was observed for cells treated with the scrambled control peptide. This indicates that the effects of the TR47-66 peptide were specific for the newly created N-tethered ligand sequence of PAR1 after cleavage at Arg46.

Additionally, it was determined that activation of Akt by TR47-66 was dependent on PAR1 since the peptide failed to induce Akt phosphorylation at Ser473 in the presence of the PAR1 inhibitor SCH79797. Similarly, induction of Ser9-GSK3β phosphorylation by TR47-66 required PAR1 since this effect was inhibited by the PAR1 antagonist SCH79797. Thus, a peptide with the sequence of the new N-terminus of PAR1 generated upon cleavage at Arg46 induced PAR1-dependent activation of Akt and PAR1-dependent phosphorylation of GSK3β, strongly suggesting that activation of PAR1 at Arg46 creates a novel functional tethered ligand that is capable of PAR1-dependent activation of specific cell signaling pathways.

Methods: EA.hy.926 cells (ATCC: CRL-2922) were grown in 24 well plates in DMEM (Invitrogen #12430) supplemented with glutamax (Invitrogen #35050) and 10% FBS (Hyclone #35-011-CV) in a 37° C. cell incubator with a humidified atmosphere and 5% $CO_2$ in air until confluency. Cells were treated for 4 hrs with vehicle control, 50 µM NPND, 50 µM scr-NPND or 10 µM TFLL after which staurosporine (10 µM) and the Apopercentage dye (Biocolor) were added according the manufacturer's instructions. After 1 hr cells were washed with 2×1 ml PBS and 110 µl of the dye release agent was added to the cells. Subsequently 100 µl aliquots were transferred to a black 96 well plate and fluorescence was measured (530 nm excitation/580 nm emission). Apoptosis was expressed as a percentage of cells treated with 10 mM $H_2O_2$ for which apoptosis was set at 100%.

Example 7: TR47-66 Peptide Mimics Signaling Induced by APC, not that by Thrombin Further studies were performed to confirm that the TR47-66 peptide mimics APC-induced signaling but does not mimic thrombin-induced or TRAP-induced cell signaling, as indicated in the Examples above. Classical activation of PAR1 by thrombin or TRAP results in the activation of the mitogen-activated protein kinase (MAPK) pathway as typically demonstrated by rapid phosphorylation of extracellular-signal-regulated kinases 1 and 2 (ERK1/2) at Thr202 and Tyr204 or Thr185 and Tyr187, respectively. We observed that, consistent with earlier reports, APC induced a transient but modest activation of ERK1/2. Interestingly, TR47-66 failed to induce any noticeable activation of ERK1/2 under conditions where TRAP and APC did so. Thus, TR47-66 does not activate the classical PAR1 MAPK pathway that is activated by thrombin and TRAP. Remarkably, TR47-66 induced activation of Akt with a time course that mimicked APC's robust activation of Akt. In contrast and reflecting the striking functional selectivity of TR47-66 and APC, neither thrombin nor TRAP induced Ser473-Akt phosphorylation under the employed experimental conditions. Similar to activation of Akt, APC induced a sustained phosphorylation of GSK3β at Ser9, mimicking the effect of TR47-66. Unlike this effect of APC and TR47-66, incubation of endothelial cells with TRAP did not result in Ser9-GSK3β phosphorylation. Together these signaling data indicated that the N-terminus generated by cleavage of PAR1 at Arg41 causes activation of the MAPK pathway whereas the N-terminus generated by cleavage of PAR1 at Arg46 causes activation of the Akt pathway. Thus, the different N-termini that arise from different cleavages of PAR1 by APC are biased agonists with remarkable functional selectivity.

Example 8: TR47-66 Induced Vascular-Endothelial Protective Effects In Vitro and In Vivo Employing β-arrestin-mediated signaling versus G protein-dependent signaling is a hallmark of biased signaling by GPCRs. Recently, PAR1 was shown to exhibit biased signaling because activation of Rac1 by APC and APC-mediated endothelial barrier protection requires β-arrestin-2 and dishevelled-2 scaffolding whereas thrombin-induced vascular leakage and RhoA activation requires G proteins but not β-arrestins (Soh et al., Proc. Natl. Acad. Sci. U.S.A 2011; 108:E1372-E1380). Consistently, we observed that the TR47-66 peptide but not the scrTR47 control peptide induced APC-like activation of Rac1. We also observed that, mimicking the well known vasculoprotective activity of APC, the TR47-66 peptide protected confluent endothelial barriers against thrombin-induced permeability, whereas the control scrTR47 peptide was without effect.

To probe whether TR47-66 could induce vascular protective effects in vivo, a modification of the modified Miles assay was used in which vascular permeability is measured by the extravasation of Evans blue dye in the skin induced by local subcutaneous injection of vascular endothelial growth factor (VEGF)165. Immunocompetent SKH1 hairless mice were used to avoid the need for hair removal that often can result in artifactual leakage due to inflammation of the skin. Evans blue extravasation in the skin was quantified using the Odyssey near-infrared fluorescent imager at 700 nm. TR47-66 peptide or the control scrTR47 peptide were injected i.v. in the retro-orbital sinus 5 min before local subcutaneous injection of recombinant murine VEGF or BSA control and 30 min after i.v. administration of Evans blue. In the absence of TR47-66 (PBS control), VEGF induced clearly distinguishable areas of Evans blue extravasation, whereas after injection of BSA vehicle control only the needle points marking the injection site could be observed. Quantification of Evans blue extravasation by near infrared fluorescence at 700 nm eliminated the time consuming need for Evans blue extraction from punch biopsy and provided reliable and reproducible results. The TR47-66 peptide significantly decreased vascular leakage by 45% compared to PBS control, whereas vascular leakage in the presence of the scrTR47 control peptide was indiscriminate from PBS control. Neither TR47-66 nor scrTR47 affected vascular leakage in the absence of VEGF. Thus, like APC, the TR47 peptide causes activation of Rac1, stabilizes endothelial barriers in vitro, and in vivo can markedly reduce vascular leakage.

Some assays employed in this study were performed as follow. Rad activation. The pGEXTK-PAK1 70-117 construct encoding a GST fusion to p21-activated kinase (PAK-1)-binding domain (PBD) was kindly made available by Dr. J Chernoff (Addgene plasmid 12217). GST-PAK1 was purified from transformed BL21 (DE3) *Escherichia coli* using B-Per lysis buffer (Pierce) with lysozyme, DNAse I and Halt EDTA-free protease inhibitor cocktail (Pierce) on Glutathione-agarose according to the manufacturer's recommendation. Pull down of active Rac1 was performed as described in Pellegrin et al., *Curr. Protoc. Cell Biol.* 2008; Chapter 14: Unit 14.8. Briefly, endothelial EA.hy.926 cells ($5*10^6$ per plate) were grown in 100-mm dishes for 48 hr and serum starved overnight before addition of peptides (50 µM) for 30 or 180 min. Lysates (2 mg) were mixed with GST-PAK1 Glutathione-agarose (150 µg) and after washing active GTP-Rac1 was eluted from GST-PAK1 Glutathione-agarose by boiling in reducing SDS sample buffer (LI-COR). Active GTP-Rac1 was resolved on 12% SDS PAGE, transferred to Immobilon-FL PVDF membrane, and immunoblotted with a mouse anti-Rac1 antibody (BD Bioscience) and IRDye 800CW donkey anti-mouse secondary antibodies (LI-COR). Immunoblots were scanned on the Odyssey Imager (LI-COR). Quantification of integrated fluorescence intensity (K counts) was done using Odyssey Application Software v3.0 (LI-COR).

Endothelial Barrier Protection.

Permeability of endothelial cell barrier function was determined as described with minor modifications. Briefly, EA.hy.926 endothelial cells ($5*10^4$ cells/well) were grown on polycarbonate membrane Transwell inserts (Costar, 3 µm pore size, 12 mm diameter). When confluent, cells were incubated with APC (20 nM), TR47 (50 µM), or scrTR47 (50 µM) for 4 hr in serum-free media with 0.1% BSA (fatty acid poor and endotoxin free fraction V, Calbiochem). After incubation with thrombin (10 nM) for 10 min, the media in the inner chamber was replaced with complete medium containing 4% BSA and 0.67 mg/ml Evans blue. Endothelial cell permeability was determined by absorbance of Evans blue in the outer chamber at 650 nm. Permeability was expressed as the fold change in absorbance compared to that in the absence of thrombin (normalized to 1).

In Vivo Vascular Permeability Assay.

The study was approved by the Institutional Animal Care and Use Committee of The Scripps Research Institute and complied with National Institutes of Health guidelines. SKIH1-E hairless male (6 to 8 weeks old) were from Charles River Labs (Wilmington, Mass.). Vascular permeability was determined using a known VEGF-induced leakage model (Sanna et al., *Nat. Chem. Biol.* 2006; 2(8):434-441; and Miles et al., *J Physiol* 1952; 118(2):228-257) with some modifications. Briefly, 100l of a sterile-filtered solution containing 0.5% (w/v) Evans blue (Sigma) in 0.9% NaCl (Sigma) was injected in isofluran-anesthetized mice. After 30 min, 50 µL of peptides (125 µg; TR47 or scrTR47) or PBS were injected intravenously in the retro-orbital sinus of mice anesthetized with Ketamin-Xylazin (100 and 10 mg/kg, respectively). After 5 min, mice received subcutaneously 15 mL of 75 ng/injection recombinant mouse VEGF165 (BioVision, Milpitas, Calif.) in 0.1% BSA-PBS (3 sites on the right side of the abdomen) or vehicle (2 sites on the left side). After 30 min, mice were sacrificed, photographed, and Evans blue extravasation in the skin was determined using the Odyssey Imager (LI-COR Biosciences, Lincoln, Nebr.) in the 700 nm channel with 4 mm offset. Quantification of the intensity of the Evans blue dye signal was done using the Odyssey Application Software version 3.0. A mean value for 3 data points (VEGF) or 2 data points (BSA) (injection sites) was made for each mouse and normalized to the VEGF sites in PBS-injected mice. In total, 5 independent experiments were performed using a total of 23 mice (n=11 for PBS, n=6 for TR47 and n=6 for scrTR47).

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each was specifically and individually indicated to be incorporated by reference.

ADDITIONAL SEQUENCE INFORMATION

SEQ ID NO: 1. Human PAR1
```
  1 MGPRRLLLVA ACFSLCGPLL SARTRARRPE SKATNATLDP
 41 RSFLLRNPND KYEPFWEDEE KNESGLTEYR LVSINKSSPL
 81 QKQLPAFISE DASGYLTSSW LTLFVPSVYT GVFVVSLPLN
121 IMAIVVFILK MKVKKPAVVY MLHLATADVL FVSVLPFKIS
161 YYFSGSDWQF GSELCRFVTA AFYCNMYASI LLMTVISIDR
201 FLAVVYPMQS LSWRTLGRAS FTCLAIWALA IAGVVPLLLK
241 EQTIQVPGLN ITTCHDVLNE TLLEGYYAYY FSAFSAVFFF
281 VPLIISTVCY VSIIRCLSSS AVANRSKKSR ALFLSAAVFC
    IFIICFGPTN
331 VLLIAHYSFL SHTSTTEAAY FAYLLCVCVS SISCCIDPLI
371 YYYASSECQR YVYSILCCKE SSDPSSYNSS GQLMASKMDT
411 CSSNLNNSIY KKLLT
```

SEQ ID NO: 2. Human PAR1 Met$^1$-Arg$^{46}$ deleted fragment
```
 47 NPND KYEPFWEDEE
 61 KNESGLTEYR LVSINKSSPL QKQLPAFISE DASGYLTSSW
    LTLFVPSVYT
111 GVFVVSLPLN IMAIVVFILK MKVKKPAVVY MLHLATADVL
151 FVSVLPFKIS YYFSGSDWQF GSELCRFVTA AFYCNMYASI
191 LLMTVISIDR FLAVVYPMQS LSWRTLGRAS FTCLAIWALA
231 IAGVVPLLLK EQTIQVPGLN ITTCHDVLNE TLLEGYYAYY
271 FSAFSAVFFF VPLIISTVCY VSIIRCLSSS AVANRSKKSR
    ALFLSAAVFC
321 IFIICFGPTN VLLIAHYSFL SHTSTTEAAY FAYLLCVCVS
    SISCCIDPLI
371 YYYASSECQR YVYSILCCKE SSDPSSYNSS GQLMASKMDT
411 CSSNLNNSIY KKLLT
```

SEQ ID NO: 3. Human PAR1 Asn$^{47}$-Trp$^{100}$ fragment
NPND KYEPFWEDEE KNESGLTEYR LVSINKSSPL
QKQLPAFISE DASGYLTSSW

---

What is claimed is:

1. A polypeptide derived from protease activated receptor-1 (PAR1), consisting of an N-terminal fragment of human PAR1 extracellular region $Asn^{47}$-$Trp^{100}$ (SEQ ID NO:3) or conservatively modified variant thereof, wherein the fragment comprises at least the first 22 N-terminal residues of SEQ ID NO:3.

2. The polypeptide of claim 1, wherein the fragment comprises at least the first 25 N-terminal residues of human PAR1 extracellular fragment $Asn^{47}$-$Trp^{100}$ (SEQ ID NO:3).

3. The polypeptide of claim 1, wherein the fragment comprises at least the first 25 N-terminal residues that are identical to the corresponding N-terminal residues of human PAR1 extracellular region $Asn^{47}$-$Trp^{100}$ (SEQ ID NO:3).

4. The polypeptide of claim 1, consisting of an amino acid sequence shown in SEQ ID NO:3.

5. A peptide derived from protease activated receptor-1 (PAR1), consisting of 10, 11, 12, 13, 14, 16, 17, 18, 19 or 20 amino acid residues that are identical to the corresponding N-terminal residues of human PAR1 extracellular region $Asn^{47}$-$Trp^{100}$ (SEQ ID NO:3) or conservatively modified variant thereof.

6. The polypeptide of claim 5, consisting of an amino acid sequence as shown in any one of SEQ ID NOs:4-7.

7. An isolated polynucleotide encoding the polypeptide of claim 1.

8. A method of promoting cytoprotective activity for endothelial cells, comprising contacting the cells with a PAR1-derived cytoprotective polypeptide, wherein the PAR1-derived polypeptide (1) consisting of an N-terminal fragment of human PAR1 extracellular fragment $Asn^{47}$-$Trp^{100}$ (SEQ ID NO:3) or conservatively modified variant thereof, wherein the fragment comprises at least the first 22 N-terminal residues of SEQ ID NO:3 or (2) consists of an amino acid sequence that is identical to the first 6, 7, 8, 10, 11, 12, 13, 14, 16, 17, 18, 19 or 20 N-terminal residues of human PAR1 extracellular fragment $Asn^{47}$-$Trp^{100}$ (SEQ ID NO:3) or conservatively modified variant thereof.

9. The method of claim 8, wherein the polypeptide consists of an amino acid sequence as shown in SEQ ID NO:4 (NPNDKYEPFWEDEEKNESGL).

10. The method of claim 8, wherein the endothelial cells are present in a subject.

11. The method of claim 8, wherein the polypeptide is administered to a subject to reduce mortality from adult severe sepsis or pediatric meningococcemia; to promote wound healing in diabetic ulcer; to treat injuries from ischemic stroke, neurotrauma, or other acute or chronic neurodegenerative conditions; to treat injuries from cardiac ischemia/reperfusion, hepatic ischemia/reperfusion, renal ischemia/reperfusion; to treat inflammatory lung injury or gastrointestinal injury; to treat flap necrosis in reconstructive surgery; to prolong survival following Ebola infection; or to reduce injury caused by radiation.

12. The polypeptide of claim 5, consisting of an amino acid sequence as shown in SEQ ID NO:4 (NPNDKYEPFWEDEEKNESGL) or conservatively modified variant thereof.

13. A synthetic or isolated peptide derived from protease activated receptor-1 (PAR1), consisting of an amino acid sequence that is identical to the first 6, 7, or 8 N-terminal residues of the $Met^1$-$Arg^{46}$ deleted human PAR1 sequence (SEQ ID NO:2) or conservatively modified variant thereof.

14. The peptide of claim 13, consisting of NPNDKY (SEQ ID NO:14) or conservatively modified variant thereof.

15. The polypeptide of claim 5, consisting of an amino acid sequence as shown in NPNDKYEPFW (SEQ ID NO:16), NPNDKYEPFWED (SEQ ID NO:17), NPNDKYEPFWEDEE (SEQ ID NO:18), NPNDKYEPFWEDEEKN (SEQ ID NO:19) or NPNDKYEPFWEDEEKNES (SEQ ID NO:20).

16. The peptide of claim 13, consisting of NPNDKYEP (SEQ ID NO:15) or conservatively modified variant thereof.

* * * * *

SEQUENCE LISTING

<160> NUMBER OF SEQ ID NOS: 21

<210> SEQ ID NO 1
<211> LENGTH: 425
<212> TYPE: PRT
<213> ORGANISM: Homo sapiens

<400> SEQUENCE: 1

```
Met Gly Pro Arg Arg Leu Leu Val Ala Ala Cys Phe Ser Leu Cys
1               5                   10                  15

Gly Pro Leu Leu Ser Ala Arg Thr Arg Ala Arg Arg Pro Glu Ser Lys
            20                  25                  30

Ala Thr Asn Ala Thr Leu Asp Pro Arg Ser Phe Leu Leu Arg Asn Pro
        35                  40                  45

Asn Asp Lys Tyr Glu Pro Phe Trp Glu Asp Glu Glu Lys Asn Glu Ser
    50                  55                  60

Gly Leu Thr Glu Tyr Arg Leu Val Ser Ile Asn Lys Ser Ser Pro Leu
65                  70                  75                  80

Gln Lys Gln Leu Pro Ala Phe Ile Ser Glu Asp Ala Ser Gly Tyr Leu
            85                  90                  95

Thr Ser Ser Trp Leu Thr Leu Phe Val Pro Ser Val Tyr Thr Gly Val
            100                 105                 110

Phe Val Val Ser Leu Pro Leu Asn Ile Met Ala Ile Val Val Phe Ile
            115                 120                 125

Leu Lys Met Lys Val Lys Lys Pro Ala Val Val Tyr Met Leu His Leu
        130                 135                 140

Ala Thr Ala Asp Val Leu Phe Val Ser Val Leu Pro Phe Lys Ile Ser
145                 150                 155                 160

Tyr Tyr Phe Ser Gly Ser Asp Trp Gln Phe Gly Ser Glu Leu Cys Arg
            165                 170                 175
```

```
Phe Val Thr Ala Ala Phe Tyr Cys Asn Met Tyr Ala Ser Ile Leu Leu
            180                 185                 190

Met Thr Val Ile Ser Ile Asp Arg Phe Leu Ala Val Tyr Pro Met
        195                 200                 205

Gln Ser Leu Ser Trp Arg Thr Leu Gly Arg Ala Ser Phe Thr Cys Leu
        210                 215                 220

Ala Ile Trp Ala Leu Ala Ile Ala Gly Val Val Pro Leu Leu Leu Lys
225                 230                 235                 240

Glu Gln Thr Ile Gln Val Pro Gly Leu Asn Ile Thr Thr Cys His Asp
                245                 250                 255

Val Leu Asn Glu Thr Leu Leu Glu Gly Tyr Tyr Ala Tyr Tyr Phe Ser
            260                 265                 270

Ala Phe Ser Ala Val Phe Phe Phe Val Pro Leu Ile Ile Ser Thr Val
        275                 280                 285

Cys Tyr Val Ser Ile Ile Arg Cys Leu Ser Ser Ala Val Ala Asn
        290                 295                 300

Arg Ser Lys Lys Ser Arg Ala Leu Phe Leu Ser Ala Ala Val Phe Cys
305                 310                 315                 320

Ile Phe Ile Ile Cys Phe Gly Pro Thr Asn Val Leu Leu Ile Ala His
                325                 330                 335

Tyr Ser Phe Leu Ser His Thr Ser Thr Thr Glu Ala Ala Tyr Phe Ala
            340                 345                 350

Tyr Leu Leu Cys Val Cys Val Ser Ser Ile Ser Cys Cys Ile Asp Pro
        355                 360                 365

Leu Ile Tyr Tyr Tyr Ala Ser Ser Glu Cys Gln Arg Tyr Val Tyr Ser
        370                 375                 380

Ile Leu Cys Cys Lys Glu Ser Ser Asp Pro Ser Ser Tyr Asn Ser Ser
385                 390                 395                 400

Gly Gln Leu Met Ala Ser Lys Met Asp Thr Cys Ser Ser Asn Leu Asn
                405                 410                 415

Asn Ser Ile Tyr Lys Lys Leu Leu Thr
            420                 425

<210> SEQ ID NO 2
<211> LENGTH: 379
<212> TYPE: PRT
<213> ORGANISM: Homo sapiens

<400> SEQUENCE: 2

Asn Pro Asn Asp Lys Tyr Glu Pro Phe Trp Glu Asp Glu Lys Asn
1               5                   10                  15

Glu Ser Gly Leu Thr Glu Tyr Arg Leu Val Ser Ile Asn Lys Ser Ser
            20                  25                  30

Pro Leu Gln Lys Gln Leu Pro Ala Phe Ile Ser Glu Asp Ala Ser Gly
        35                  40                  45

Tyr Leu Thr Ser Ser Trp Leu Thr Leu Phe Val Pro Ser Val Tyr Thr
    50                  55                  60

Gly Val Phe Val Val Ser Leu Pro Leu Asn Ile Met Ala Ile Val Val
65                  70                  75                  80

Phe Ile Leu Lys Met Lys Val Lys Lys Pro Ala Val Val Tyr Met Leu
                85                  90                  95

His Leu Ala Thr Ala Asp Val Leu Phe Val Ser Val Leu Pro Phe Lys
            100                 105                 110

Ile Ser Tyr Tyr Phe Ser Gly Ser Asp Trp Gln Phe Gly Ser Glu Leu
```

```
            115                 120                 125
Cys Arg Phe Val Thr Ala Ala Phe Tyr Cys Asn Met Tyr Ala Ser Ile
    130                 135                 140

Leu Leu Met Thr Val Ile Ser Ile Asp Arg Phe Leu Ala Val Val Tyr
145                 150                 155                 160

Pro Met Gln Ser Leu Ser Trp Arg Thr Leu Gly Arg Ala Ser Phe Thr
                165                 170                 175

Cys Leu Ala Ile Trp Ala Leu Ala Ile Ala Gly Val Val Pro Leu Leu
            180                 185                 190

Leu Lys Glu Gln Thr Ile Gln Val Pro Gly Leu Asn Ile Thr Thr Cys
        195                 200                 205

His Asp Val Leu Asn Glu Thr Leu Leu Glu Gly Tyr Tyr Ala Tyr Tyr
    210                 215                 220

Phe Ser Ala Phe Ser Ala Val Phe Phe Val Pro Leu Ile Ile Ser
225                 230                 235                 240

Thr Val Cys Tyr Val Ser Ile Ile Arg Cys Leu Ser Ser Ser Ala Val
                245                 250                 255

Ala Asn Arg Ser Lys Lys Ser Arg Ala Leu Phe Leu Ser Ala Ala Val
            260                 265                 270

Phe Cys Ile Phe Ile Ile Cys Phe Gly Pro Thr Asn Val Leu Leu Ile
        275                 280                 285

Ala His Tyr Ser Phe Leu Ser His Thr Ser Thr Glu Ala Ala Tyr
    290                 295                 300

Phe Ala Tyr Leu Leu Cys Val Cys Val Ser Ser Ile Ser Cys Cys Ile
305                 310                 315                 320

Asp Pro Leu Ile Tyr Tyr Tyr Ala Ser Ser Glu Cys Gln Arg Tyr Val
                325                 330                 335

Tyr Ser Ile Leu Cys Cys Lys Glu Ser Ser Asp Pro Ser Ser Tyr Asn
            340                 345                 350

Ser Ser Gly Gln Leu Met Ala Ser Lys Met Asp Thr Cys Ser Ser Asn
        355                 360                 365

Leu Asn Asn Ser Ile Tyr Lys Lys Leu Leu Thr
    370                 375

<210> SEQ ID NO 3
<211> LENGTH: 54
<212> TYPE: PRT
<213> ORGANISM: Homo sapiens

<400> SEQUENCE: 3

Asn Pro Asn Asp Lys Tyr Glu Pro Phe Trp Glu Asp Glu Glu Lys Asn
1               5                   10                  15

Glu Ser Gly Leu Thr Glu Tyr Arg Leu Val Ser Ile Asn Lys Ser Ser
            20                  25                  30

Pro Leu Gln Lys Gln Leu Pro Ala Phe Ile Ser Glu Asp Ala Ser Gly
        35                  40                  45

Tyr Leu Thr Ser Ser Trp
    50

<210> SEQ ID NO 4
<211> LENGTH: 20
<212> TYPE: PRT
<213> ORGANISM: Homo sapiens

<400> SEQUENCE: 4

Asn Pro Asn Asp Lys Tyr Glu Pro Phe Trp Glu Asp Glu Glu Lys Asn
```

```
                1               5                  10                 15
Glu Ser Gly Leu
            20

<210> SEQ ID NO 5
<211> LENGTH: 20
<212> TYPE: PRT
<213> ORGANISM: Artificial Sequence
<220> FEATURE:
<223> OTHER INFORMATION: modified with substituted residues

<400> SEQUENCE: 5

Asn Pro Asn Asp Arg Tyr Glu Pro Phe Trp Glu Asp Glu Glu Lys Asn
1               5                  10                 15

Glu Ser Gly Leu
            20

<210> SEQ ID NO 6
<211> LENGTH: 21
<212> TYPE: PRT
<213> ORGANISM: Artificial Sequence
<220> FEATURE:
<223> OTHER INFORMATION: modified with replacement residues

<400> SEQUENCE: 6

Asn Pro Asn Asp Lys Tyr Glu Pro Phe Trp Glu Glu Asp Glu Glu Lys
1               5                  10                 15

Asn Glu Ser Gly Leu
            20

<210> SEQ ID NO 7
<211> LENGTH: 20
<212> TYPE: PRT
<213> ORGANISM: Artificial Sequence
<220> FEATURE:
<223> OTHER INFORMATION: modified with replacement residues

<400> SEQUENCE: 7

Asn Pro Asn Asp Arg Tyr Glu Pro Phe Trp Glu Asp Glu Asp Lys Asn
1               5                  10                 15

Glu Ser Gly Leu
            20

<210> SEQ ID NO 8
<211> LENGTH: 10
<212> TYPE: PRT
<213> ORGANISM: Artificial Sequence
<220> FEATURE:
<223> OTHER INFORMATION: modified with replacement residues

<400> SEQUENCE: 8

Thr Phe Leu Leu Arg Asn Pro Asn Asp Lys
1               5                  10

<210> SEQ ID NO 9
<211> LENGTH: 20
<212> TYPE: PRT
<213> ORGANISM: Artificial Sequence
<220> FEATURE:
<223> OTHER INFORMATION: scrambled sequence

<400> SEQUENCE: 9

Gly Asp Glu Asn Glu Asn Glu Lys Pro Asn Trp Tyr Glu Leu Lys Glu
1               5                  10                 15
```

Pro Asp Ser Phe
            20

<210> SEQ ID NO 10
<211> LENGTH: 18
<212> TYPE: PRT
<213> ORGANISM: Homo sapiens

<400> SEQUENCE: 10

Thr Arg Ala Arg Arg Pro Glu Ser Lys Ala Thr Asn Ala Thr Leu Asp
1               5                   10                  15

Pro Arg

<210> SEQ ID NO 11
<211> LENGTH: 23
<212> TYPE: PRT
<213> ORGANISM: Homo sapiens

<400> SEQUENCE: 11

Thr Arg Ala Arg Arg Pro Glu Ser Lys Ala Thr Asn Ala Thr Leu Asp
1               5                   10                  15

Pro Arg Ser Phe Leu Leu Arg
            20

<210> SEQ ID NO 12
<211> LENGTH: 25
<212> TYPE: PRT
<213> ORGANISM: Homo sapiens

<400> SEQUENCE: 12

Ser Phe Leu Leu Arg Asn Pro Asn Asp Lys Tyr Glu Pro Phe Trp Glu
1               5                   10                  15

Asp Glu Glu Lys Asn Glu Ser Gly Leu
            20                  25

<210> SEQ ID NO 13
<211> LENGTH: 30
<212> TYPE: PRT
<213> ORGANISM: Homo sapiens

<400> SEQUENCE: 13

Ala Thr Asn Ala Thr Leu Asp Pro Arg Ser Phe Leu Leu Arg Asn Pro
1               5                   10                  15

Asn Asp Lys Tyr Glu Pro Phe Trp Glu Asp Glu Glu Lys Asn
            20                  25                  30

<210> SEQ ID NO 14
<211> LENGTH: 6
<212> TYPE: PRT
<213> ORGANISM: Homo sapiens

<400> SEQUENCE: 14

Asn Pro Asn Asp Lys Tyr
1               5

<210> SEQ ID NO 15
<211> LENGTH: 8
<212> TYPE: PRT
<213> ORGANISM: Homo sapiens

<400> SEQUENCE: 15

Asn Pro Asn Asp Lys Tyr Glu Pro
1               5

```
<210> SEQ ID NO 16
<211> LENGTH: 10
<212> TYPE: PRT
<213> ORGANISM: Homo sapiens

<400> SEQUENCE: 16

Asn Pro Asn Asp Lys Tyr Glu Pro Phe Trp
1               5                   10

<210> SEQ ID NO 17
<211> LENGTH: 12
<212> TYPE: PRT
<213> ORGANISM: Homo sapiens

<400> SEQUENCE: 17

Asn Pro Asn Asp Lys Tyr Glu Pro Phe Trp Glu Asp
1               5                   10

<210> SEQ ID NO 18
<211> LENGTH: 14
<212> TYPE: PRT
<213> ORGANISM: Homo sapiens

<400> SEQUENCE: 18

Asn Pro Asn Asp Lys Tyr Glu Pro Phe Trp Glu Asp Glu Glu
1               5                   10

<210> SEQ ID NO 19
<211> LENGTH: 16
<212> TYPE: PRT
<213> ORGANISM: Homo sapiens

<400> SEQUENCE: 19

Asn Pro Asn Asp Lys Tyr Glu Pro Phe Trp Glu Asp Glu Glu Lys Asn
1               5                   10                  15

<210> SEQ ID NO 20
<211> LENGTH: 18
<212> TYPE: PRT
<213> ORGANISM: Homo sapiens

<400> SEQUENCE: 20

Asn Pro Asn Asp Lys Tyr Glu Pro Phe Trp Glu Asp Glu Glu Lys Asn
1               5                   10                  15

Glu Ser

<210> SEQ ID NO 21
<211> LENGTH: 6
<212> TYPE: PRT
<213> ORGANISM: Homo sapiens

<400> SEQUENCE: 21

Ser Phe Leu Leu Arg Asn
1               5
```